(12) United States Patent
Schäfer et al.

(10) Patent No.: US 6,448,205 B1
(45) Date of Patent: Sep. 10, 2002

(54) SUBSTITUTED 2-PHENYLPYRIDINE AS HERBICIDE

(75) Inventors: Peter Schäfer, Ottersheim; Michael Rack, Heidelberg; Gerhard Hamprecht, Weinheim; Helmut Walter, Obrigheim; Karl-Otto Westphalen, Speyer; Ulf Misslitz, Neustadt; Markus Menges, Mannheim; Cyrill Zagar, Ludwigshafen; Olaf Menke, Altleiningen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/242,463

(22) PCT Filed: Aug. 13, 1997

(86) PCT No.: PCT/EP97/04420
§ 371 (c)(1),
(2), (4) Date: Feb. 17, 1999

(87) PCT Pub. No.: WO98/07700
PCT Pub. Date: Feb. 26, 1998

(30) Foreign Application Priority Data

Aug. 22, 1996 (DE) .......................... 196 33 746

(51) Int. Cl.$^7$ .................. A01N 43/40; C07D 213/89
(52) U.S. Cl. ............... 504/254; 504/244; 504/255; 546/290; 546/293; 546/294; 546/345
(58) Field of Search ................ 546/290, 293, 546/294, 345; 504/254, 244, 255

(56) References Cited

U.S. PATENT DOCUMENTS

| | | | |
|---|---|---|---|
| 3,850,576 A | 11/1974 | Rittersdorf et al. | 23/230 |
| 4,405,552 A | 9/1983 | Miesel | 424/263 |
| 5,733,850 A | 3/1998 | Schaefer et al. | 504/244 |
| 5,747,422 A | 5/1998 | Schaefer et al. | 504/244 |
| 5,783,522 A * | 7/1998 | Schaefer et al. | 504/294 |

FOREIGN PATENT DOCUMENTS

| | | |
|---|---|---|
| CA | 2126072 | 5/1994 |
| DE | 4323916 | * 7/1996 |
| DE | 19500760 | * 7/1996 |
| DE | 19500911 | * 7/1996 |
| DE | 19610571 | 9/1997 |
| EP | 147105 | 7/1985 |
| WO | 94/05153 | 3/1994 |
| WO | 95/02590 | 1/1995 |
| WO | 97/06143 | 2/1997 |
| WO | 97/11059 | 3/1997 |
| WO | 97/30059 | 8/1997 |

OTHER PUBLICATIONS

Bull. Chem. Soc. Japan, vol. 63, No. 10 pp. 2820–2827, Yasuo Tohda et al, Nucleophic Reaction . . . , 1990.*
J. Med. Chem., 16, 319–327, 1973.
J. Med. Chem., 29, 427–433, 1986.
Bull. Soc. Chim. Belg., 95, 1009–1020, 1986.
J. Med. Chem., 14(4), 1971, 339–344.

* cited by examiner

Primary Examiner—Alan L. Rotman
Assistant Examiner—Rita Desai
(74) Attorney, Agent, or Firm—Keil & Weinkauf

(57) ABSTRACT

Substituted 2-phenylpyridines of formula I

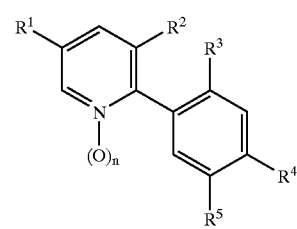

where $R^1$ to $R^5$ are described herein,
their use as herbicides and for the desiccation and/or defoliation of plants.

10 Claims, No Drawings

SUBSTITUTED 2-PHENYLPYRIDINE AS HERBICIDE

The present invention relates to novel substituted 2-phenyl-pyridines of the formula I

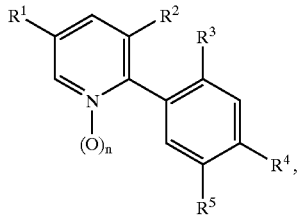

in which the variables have the following meanings:
n is zero or 1;
R$^1$ is mercapto, hydroxysulfonyl, chlorosulfonyl, aminosulfonyl, $C_1$–$C_6$-alkylthio, $C_1$–$C_6$-alkylsulfinyl, $C_1$–$C_6$-alkylsulfonyl, $C_1$–$C_6$-alkylaminosulfonyl or di($C_1$–$C_6$-alkyl)aminosulfonyl;
R$^2$,R$^3$ independently of one another are hydrogen or halogen;
R$^4$ is cyano, hydroxyl, halogen, $C_1$–$C_6$-alkoxy or phenylmethoxy, it being possible for the phenyl ring to be unsubstituted or to have attached to it one to three substituents, in each case selected from the group consisting of hydroxyl, halogen, $C_1$–$C_6$-alkyl, $C_1$–$C_6$-haloalkyl, $C_1$–$C_6$-alkoxy, $C_1$–$C_6$-haloalkoxy, hydroxycarbonyl, ($C_1$–$C_6$-alkoxy)carbonyl and ($C_1$–$C_6$-alkoxy)carbonyl-$C_1$–$C_6$-alkoxy;
R$^5$ is hydrogen, nitro, cyano, hydroxylamino, halogen, $C_1$–$C_6$-alkyl, $C_1$–$C_6$-haloalkyl, —COCl, —CO—OR$^6$, —CO—N(R$^7$)R$^8$, —CO—O—($C_1$–$C_4$-alkylene)—CO—R$^6$, —CO—O—($C_1$–$C_4$-alkylene)—CO—N(R$^7$)R$^8$, —X$^1$—($C_1$–$C_4$-alkylene)—CO—R$^6$, —X$^1$—($C_1$–$C_4$-alkylene)—CO—OR$^6$, —X$^1$—($C_1$–$C_4$-alkylene)—CO—O—($C_1$–$C_4$-alkylene)—CO—OR$^6$, —X$^1$—($C_1$–$C_4$-alkylene)—CO—N(R$^7$)R$^8$, —X$^1$—R$^9$, —CH=C(R$^{10}$)—CO—OR$^6$, —CH=C(R$^{10}$)—CO—O—($C_1$–$C_4$-alkylene)—CO—OR$^6$, —CH=C(R$^{10}$)—CO—N(R$^7$)R$^8$, formyl, —CO—R$^6$,

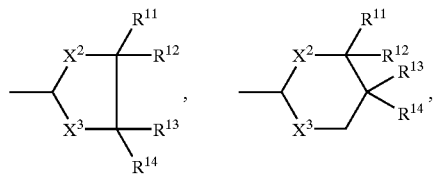

—C(R$^8$)=N—OR$^{15}$, —X$^1$—($C_1$–$C_4$-alkylene)—C(R$^8$)=N—OR$^{15}$, —CH=C(R$^{10}$)—C(R$^8$)=N—OR$^{15}$, —CH($C_1$–$C_6$-alkoxy)$_2$, —N(R$^{16}$)R$^{17}$, —N(R$^{16}$)—SO$_2$—($C_1$–$C_6$-alkyl), —N(R$^{16}$)—CO—($C_1$–$C_6$-alkyl), chlorosulfonyl, hydroxysulfonyl or —SO$_2$—N(R$^{18}$)R$^{19}$;
R$^6$ is hydrogen, $C_1$–$C_6$-alkyl, $C_1$–$C_6$-haloalkyl, $C_3$–$C_6$-alkenyl, $C_3$–$C_6$-alkynyl, $C_3$–$C_6$-cycloalkyl, $C_1$–$C_6$-alkoxy-$C_1$–$C_6$-alkyl or 3-oxetanyl;
R$^7$ is hydrogen or $C_1$–$C_6$-alkyl;
R$^8$ is hydrogen, hydroxyl, $C_1$–$C_6$-alkyl, hydroxycarbonyl-$C_1$–$C_6$-alkyl, ($C_1$–$C_6$-alkoxy)carbonyl-$C_1$–$C_6$-alkyl, $C_1$–$C_6$-alkoxy, $C_1$–$C_6$-haloalkoxy, phenyl-$C_1$–$C_6$-alkoxy, $C_3$–$C_6$-alkenyloxy or $C_3$–$C_6$-alkynyloxy or R$^7$ and R$^8$ together are a tetra- or pentamethylene chain which can have attached to it a ($C_1$–$C_6$-alkoxy)carbonyl radical;
R$^9$ is hydrogen, $C_1$–$C_6$-alkyl, $C_1$–$C_6$-haloalkyl, $C_3$–$C_6$-alkenyl, $C_3$–$C_6$-alkynyl, $C_3$–$C_6$-cycloalkyl or $C_1$–$C_6$-alkoxy-$C_1$–$C_6$-alkyl;
R$^{10}$ is hydrogen, halogen or $C_1$–$C_6$-alkyl;
R$^{11}$–R$^{14}$ independently of one another are hydrogen, $C_1$–$C_6$-alkyl or ($C_1$–$C_6$-alkoxy)carbonyl;
R$^{15}$ is hydrogen, $C_1$–$C_6$-alkyl, phenyl-$C_1$–$C_6$-alkyl, ($C_1$–$C_6$-alkoxy)carbonyl-$C_1$–$C_6$-alkyl, $C_3$–$C_6$-alkenyl or $C_3$–$C_6$-alkynyl;
R$^{16}$ is hydrogen or $C_1$–$C_6$-alkyl;
R$^{17}$ is hydrogen, $C_1$–$C_6$-alkyl, hydroxycarbonyl-$C_1$–$C_6$-alkyl, ($C_1$–$C_6$-alkoxy)carbonyl-$C_1$–$C_6$-alkyl or $C_1$–$C_6$-alkoxy;
R$^{18}$ is hydrogen or $C_1$–$C_6$-alkyl;
R$^{19}$ is hydrogen, $C_1$–$C_6$-alkyl, hydroxycarbonyl-$C_1$–$C_6$-alkyl, ($C_1$–$C_6$-alkoxy)carbonyl-$C_1$–$C_6$-alkyl or $C_1$–$C_6$-alkoxy or
R$^{18}$ and R$^{19}$ together are a tetra- or pentamethylene chain which can have attached to it a ($C_1$–$C_6$-alkoxy)carbonyl radical;
X$^1$–X$^3$ independently of one another are oxygen or sulfur, and to the agriculturally useful salts of the compounds I where R$^6$ =hydrogen.

Moreover, the invention relates to
the use of the compounds I as herbicides or for the desiccation/defoliation of plants,
herbicidal compositions and compositions for the desiccation and/or defoliation of plants which comprise the compounds I as active substances,
methods of controlling undesirable vegetation and for the desiccation and/or defoliation of plants using the compounds I,
processes for the preparation of the compounds I and of herbicidal compositions and compositions for the desiccation and/or defoliation of plants which make use of the compounds I, and to
intermediates of the formulae IIa, V and VI.

WO 95/02580 describes a large number of herbicidally active 2-phenylpyridines. The general formula in this publication also embraces some of the present compounds I where R$^1$=$C_1$–$C_4$-alkylthio.

WO 94/05153 relates to herbicidally active benzene compounds which can also have attached to them, inter alia, a pyridine ring which is substituted by halogen and methylthio. However, the specific substitution pattern of the present 2-phenylpyridines cannot be found in this publication.

DE-A 19 500 760, DE-A 19 500 758 and DE-A 19 500 911 already describe certain substituted 2-phenylpyridines of the type of the compounds I where mercapto, $C_1$–$C_4$-alkylthio, $C_1$–$C_4$-alkylsulfinyl or $C_1$–$C_4$-alkylsulfonyl occupy the 5-position of the pyridine ring as herbicidal and desiccant/defoliant active ingredients.

However, the herbicidal activity of the known compounds is not always entirely satisfactory with regard to the harmful plants.

It is an object of the present invention to provide novel herbicidally active compounds with which undesirable plants can be controlled better, in a targeted fashion, than was possible to date. It was also an object to provide novel compounds which have a desiccant/defoliant action.

We have found that this object is achieved by the substituted 2-phenylpyridines of the formula I defined at the outset which have a herbicidal action, and by novel intermediates V and VI for their preparation.

We have furthermore found herbicidal compositions which comprise the compounds I and which have a very good herbicidal activity. Moreover, we have found processes for the preparation of these compositions and methods for controlling undesirable vegetation using the compounds I.

Moreover, we have found that the compounds I are also suitable for the defoliation/desiccation of parts of plants, suitable plants being crop plants such as cotton, potatoes, oilseed rape, sunflowers, soya beans or field beans, in particular cotton and potatoes. Accordingly, we have found compositions for the desiccation and/or defoliation of plants, processes for the preparation of these compositions, and methods for the desiccation and/or defoliation of plants using the compounds I.

Depending on the substitution pattern, the compounds of the formula I can have one or more chiral centers, in which case they are present as enantiomer or diastereomer mixtures. The invention relates not only to the pure enantiomers or diastereomers, but also to mixtures of these.

The substituted 2-phenylpyridines I where $R^6$=hydrogen can exist in the form of their agriculturally useful salts, the nature of the salt generally being of no importance. In general, suitable salts are salts of those bases where the herbicidal activity is not adversely affected in comparison with the free compound I.

Especially suitable salts are those of the alkali metals, preferably sodium and potassium salts, the alkaline earth metals, preferably calcium and magnesium salts, those of the transition metals, preferably zinc and iron salts, and also ammonium salts where the ammonium ion can, if desired, have attached to it one to four $C_1$–$C_4$-alkyl, hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, furthermore phosphonium salts, sulfonium salts such as, preferably, tri($C_1$–$C_4$-alkyl)sulfonium salts, and sulfoxonium salts such as, preferably, tri($C_1$–$C_4$-alkyl)sulfoxonium salts.

The organic moieties mentioned for the substituents $R^1$ and $R^4$ to $R^{19}$ or as radicals on a phenyl ring or on tetra- or pentamethylene are collective terms for individual enumerations of the individual group members. All carbon chains, ie. all alkyl, haloalkyl, phenylalkyl, alkylene, alkoxy, haloalkoxy, phenylalkoxy, alkylthio, alkylsulfinyl, alkylsulfonyl, hydroxycarbonylalkyl, alkoxycarbonyl, alkylamino, alkenyl, alkynyl, alkenyloxy and alkynyloxy moieties can be straight-chain or branched. Halogenated substituents preferably have attached to them one to five identical or different halogen atoms.

The meaning halogen is in each case fluorine, chlorine, bromine or iodine, in particular fluorine or chlorine.

Other examples of meanings are:

$C_1$–$C_6$-alkyl: $C_1$–$C_4$-alkyl such as $CH_3$, $C_2H_5$, n-propyl, $CH(CH_3)_2$, n-butyl, $CH(CH_3)$—$C_2H_5$, $CH_2$—CH$(CH_3)_2$ and $C(CH_3)_3$, or e.g. n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $CH_3$, $C_2H_5$, n-propyl, $CH(CH_3)_2$, n-butyl, $C(CH_3)_3$, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, eg. $CH_2F$, $CHF_2$, $CF_3$, $CH_2Cl$, $CH(Cl)_2$, $C(Cl)_3$, $CHFCl$, $CF(Cl)_2$, $CF_2Cl$, $CF_2Br$, 1-fluoroethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 1,2-dichloroethyl, 2,2,2-trichloroethyl, $C_2$—$F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, $CF_2$—$C_2F_5$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, 5,5,5-trichloropentyl, undecafluoropentyl, 6-fluorohexyl, 6-chlprohexyl, 6-bromohexyl, 6-iodohexyl, 6,6,6-trichlorohexyl or dodecafluorohexyl, in particular $CH_2F$, $CHF_2$, $CF_3$, $CH_2Cl$, 2-fluoroethyl, 2-chloroethyl, 1,2-dichloroethyl, 2,2,2-trifluoroethyl or $C_2F_5$;

phenyl-$C_1$–$C_6$-alkyl: eg. benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-benzyleth-1-yl, 1-benzyl-1-methyleth-1-yl, 1-benzylprop-1-yl or 2-phenylhex-6-yl, in particular benzyl or 2-phenylethyl;

$C_3$–$C_6$-cycloalkyl: cyclopropyl, cyclobutyl, cyclopentyl or cyclohexyl, in particular cyclopentyl or cyclohexyl;

$C_1$–$C_4$-alkylene: —$CH_2$—, —$CH(CH_3)$—, 1,2-ethylene, 1,1-propylene, 1,2-propylene, 1,3-propylene, —$C(CH_3)_2$—, 1,1-butylene, 1,2-butylene, 1,3-butylene, 1,4-butylene, 2,2-butylene, 2,3-butylene, 2-methyl-1,1-propylene, 2-methyl-1,2-propylene or 2-methyl-1,3-propylene, preferably methylene, 1,1-ethylene, 1,2-ethylene, 1,1-propylene or 2,2-propylene;

$C_1$–$C_6$-alkoxy: eg. $OCH_3$, $OC_2H_5$, n-propoxy, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular $OCH_3$, $OC_2H_5$, $OCH(CH_3)_2$ or $OC(CH_3)_3$;

$C_1$–$C_6$-haloalkoxy: $C_1$–$C_6$-alkoxy as mentioned above which is partially or fully substituted by fluorine, chlorine, bromine and/or iodine, eg. $OCH_2F$, $OCHF_2$, $OCF_3$, $OCH_2Cl$, $OCH(Cl)_2$, $OC(Cl)_3$, $OCHFCl$, $OCF(Cl)_2$, $OCF_2Cl$, $OCF_2Br$, 1-fluoroethoxy, 2-fluoroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, $OCF_2$-$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy, 5nonafluorobutoxy, 5-fluoropentoxy, 5-chloropentoxy, 5-bromopentoxy, 5-iodopentoxy, undecafluoropentoxy, 6-fluorohexyloxy, 6-chlorohexyloxy, 6-bromohexyloxy or dodecafluorohexyloxy;

phenyl-$C_1$–$C_6$-alkoxy: e.g. benzyloxy, 1-phenylethoxy, 2-phenylethoxy, 1-phenylprop-1-yloxy, 2-phenylprop-1-yloxy, 3-phenylprop-1-yloxy, 1-phenylbut-1-yloxy, 2-phenylbut-1-yloxy, 3-phenylbut-1-yloxy, 4-phenylbut-1-yloxy, 1-phenylbut-2-yloxy, 2-phenylbut-2-yloxy, 3-phenylbut-2-yloxy, 4-phenylbut-2-yloxy, 1-benzyleth-1-yloxy, 1-benzyl-1-methyl-eth-1-yloxy, 1-benzylprop-1-yloxy or 2-phenylhex-6-yloxy, in particular benzyloxy or 2-phenylethoxy;

$C_1$–$C_6$-alkoxy-$C_1$–$C_6$-alkyl: $C_1$–$C_6$-alkyl which is substituted by $C_1$–$C_6$-alkoxy as mentioned above, eg. $CH_2OCH_3$, $CH_2OC_2H_5$, $CH_2OCH_2$—$C_2H_5$, $CH_2OCH(CH_3)_2$, $CH_2OCH_2CH_2$—$C_2H_5$, (1-propoxy)methyl, (2-methyl-propoxy)methyl, $CH_2OC(CH_3)_3$, $CH_2O(CH_2)_3$—$C_2H_5$, $CH_2O(CH_2)_4$—$C_2H_5$, $CH(CH_3)OCH_3$, $CH(CH_3)OC_2H_5$, $CH_2CH_2OCH_3$, $CH_2CH_2OC_2H_5$, $CH_2CH_2OCH_2$—$C_2H_5$, $CH_2CH_2OCH(CH_3)_2$, $CH_2CH_2OCH_2CH_2$—$C_2H_5$, 2-(1-methylpropoxy)ethyl, 2-(2-methylpropoxy)ethyl, $CH_2CH_2OC(CH_3)_3$, $CH_2CH_2O(CH_2)_3$—$C_2H_5$, $CH_2CH_2O(CH_2)_4$—$C_2H_5$, 2-($OCH_3$)propyl, 2-($OC_2H_5$)propyl, 2-($OCH_2$—$C_2H_5$)propyl, 2-[$OCH(CH_3)_2$]propyl, 2-($OCH_2CH_2$—$C_2H_5$)propyl, 2-(1-methylpropoxy)propyl, 2-(2-methylpropoxy)propyl, 2-[$OC(CH_3)_3$]propyl, 3-($OCH_3$)propyl, 3-($OC_2H_5$)propyl, 3-($OCH_2$—$C_2H_5$)propyl, 3-[$OCH(CH_3)_2$]propyl, 3-($OCH_2CH_2$—$C_2H_5$)propyl, 3-(1-methylpropoxy)propyl, 3-(2-methylpropoxy)propyl, 3-[$OC(CH_3)_3$]propyl, 3-[$O(CH_2)_3$—$C_2H_5$]propyl, 3-[$O(CH_2)_4$—$C_2H_5$]propyl, 2-($OCH_3$)butyl, 2-($OC_2H_5$)butyl, 2-($OCH_2$—$C_2H_5$)butyl, 2-[$OCH(CH_3)_2$]butyl, 2-($OCH_2CH_2$—$C_2H_5$)butyl, 2-(1-methylpropoxy)butyl, 2-(2-methylpropoxy)butyl, 2-[$OC(CH_3)_3$]butyl, 3-($OCH_3$)butyl, 3-($OC_2H_5$)butyl, 3-($OCH_2$—$C_2H_5$)butyl, 3-[$OCH(CH_3)_2$]butyl, 3-($OCH_2CH_2$—$C_2H_5$)butyl, 3-(1-methylpropoxy)butyl, 3-(2-methylpropoxy)butyl, 3-[$OC(CH_3)_3$]butyl, 4-($OCH_3$)butyl, 4-($OC_2H_5$)butyl, 4-($OCH_2$—$C_2H_5$)butyl, 4-[$OCH(CH_3)_2$]butyl, 4-($OCH_2CH_2$—$C_2H_5$)butyl, 4-(1-methylpropoxy)butyl, 4-(2-methylpropoxy)butyl, 4-[$OC(CH_3)_3$]butyl, 4-[$O(CH_2)_3$—$C_2H_5$]butyl, 4-[$O(CH_2)_4$—$C_2H_5$]butyl, 5-($OCH_3$)pentyl, 5-($OC_2H_5$)pentyl, 5-($OCH_2$—$C_2H_5$)pentyl, 5-[$OCH(CH_3)_2$]pentyl, 5-($OCH_2CH_2$—$C_2H_5$)pentyl, 5-(1-methylpropoxy)pentyl, 5-(2-methylpropoxy)pentyl, 5-[$OC(CH_3)_3$]pentyl, 5-[$O(CH_2)_3$—$C_2H_5$]pentyl, 5-[$O(CH_2)_4$—$C_2H_5$]pentyl, 6-($OCH_3$)hexyl, 6-($OC_2H_5$)hexyl, 6-($OCH_2$—$C_2H_5$)hexyl, 6-[$OCH(CH_3)_2$]hexyl, 6-($OCH_2CH_2$—$C_2H_5$)hexyl, 6-(1-methylpropoxy)hexyl, 6-(2-methylpropoxy)hexyl, 6-[$OC(CH_3)_3$]hexyl, 6-[$O(CH_2)_3$—$C_2H_5$]hexyl or 6-[$O(CH_2)_4$—$C_2H_5$]hexyl, in particular $CH_2OCH_3$, $CH(CH_3)OCH_3$, $CH_3CH_2OCH_3$ or $CH(CH_3)CH_2OCH_3$;

hydroxycarbonyl-$C_1$–$C_6$-alkyl: eg. $CH_2COOH$, $CH(CH_3)COOH$, $CH_2CH_2COOH$, 1-(COOH)prop-1-yl, 2-(COOH)prop-1-yl, 3-(COOH)prop-1-yl, 1-(COOH)but-1-yl, 2-(COOH)but-1-yl, 3-(COOH)but-1-yl, 4-(COOH)but-1-yl 1-(COOH)but-2-yl, 2-(COOH)but-2-yl, 3-(COOH)but-2-yl, 4-(COOH)but-2-yl, 1-($CH_2COOH$)eth-1-yl, 1-($CH_2COOH$)-1-($CH_3$)-eth-1-yl, 1-($CH_2COOH$)prop-1-yl, 5-(COOH)pent-1-yl or 6-(COOH)hex-1-yl;

($C_1$–$C_6$-alkoxy)carbonyl: $COOCH_3$, $COOC_2H_5$, n-propoxycarbonyl, $OCH(CH_3)_2$, n-butoxycarbonyl, 1-methylpropoxycarbonyl, 2-methylpropoxycarbonyl, $OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexyloxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-$C_2H_5$-1-$CH_3$-propoxycarbonyl or 1-$C_2H_5$-2-$CH_3$-propoxycarbonyl, in particular $COOCH_3$, $COOC_2H_5$ or $COOC(CH_3)_3$;

($C_1$–$C_6$-alkoxy)carbonyl-$C_1$–$C_6$-alkyl: $C_1$–$C_6$-alkyl which is substituted by ($C_1$–$C_6$-alkoxy)carbonyl as mentioned above, eg. $CH_2COOCH_3$, $CH_2COOC_2H_5$, $CH_2COOCH_2$—$C_2H_5$, $CH_2COOCH(CH_3)_2$, $CH_2COOCH_2CH_2$—$C_2H_5$, (1-methylpropoxycarbonyl)methyl, (2-methylpropoxycarbonyl)methyl, $CH_2COOC(CH_3)_3$, $CH_2COO(CH_2)_3$—$C_2H_5$, $CH_2COO(CH_2)_4$—$C_2H_5$, $CH(CH_3)COOCH_3$, $CH(CH_3)COOC_2H_5$, $CH_2CH_2COOCH_3$, $CH_2CH_2COOC_2H_5$, $CH_2CH_2COOCH_2$—$C_2H_5$, $CH_2CH_2COOCH(CH_3)_2$, $CH_2CH_2COOCH_2CH_2$—$C_2H_5$, 2-(1-methylpropoxycarbonyl)ethyl, 2-(2-methylpropoxycarbonyl)ethyl, $CH_2CH_2COOC(CH_3)_3$, $CH_2CH_2COO(CH_2)_3$—$C_2H_5$, $CH_2CH_2COO(CH_2)_4$—$C_2H_5$, 2-($COOCH_3$)propyl, 2-($COOC_2H_5$)propyl, 2-($COOCH_2$—$C_2H_5$)propyl, 2-[$COOCH(CH_3)_2$]propyl, 2-($COOCH_2CH_2$—$C_2H_5$)propyl, 2-(1-methylpropoxycarbonyl)propyl, 2-(2-methylpropoxycarbonyl)propyl, 2-[$COOC(CH_3)_3$]propyl, 3-($COOCH_3$)propyl, 3-($COOC_2H_5$)propyl, 3-($COOCH_2$—$C_2H_5$)propyl, 3-[$COOCH(CH_3)_2$]propyl, 3-($COOCH_2CH_2$—$C_2H_5$)propyl, 3-(1-methylpropoxycarbonyl)propyl, 3-(2-methylpropoxycarbonyl)propyl, 3-[$COOC(CH_3)_3$]propyl, 3-[$COO(CH_2)_3$—$C_2H_5$]propyl, 3-[$COO(CH_2)_4$—$C_2H_5$]propyl, 2-($COOCH_3$)butyl, 2-($COOC_2H_5$)butyl, 2-($COOCH_2$—$C_2H_5$)butyl, 2-[$COOCH(CH_3)_2$]butyl, 2-($COOCH_2CH_2$—$C_2H_5$)butyl, 2-(1-methylpropoxycarbonyl)butyl, 2-(2-methylpropoxycarbonyl)butyl, 2-[$COOC(CH_3)_3$]butyl, 3-($COOCH_3$)butyl, 3-($COOC_2H_5$)butyl, 3-($COOCH_2$—$C_2H_5$)butyl, 3-[$COOCH(CH_3)_2$]butyl, 3-($COOCH_2CH_2$—$C_2H_5$)butyl, 3-(1-methylpropoxycarbonyl)butyl, 3-(2-methylpropoxycarbonyl)butyl, 3-[$COOC(CH_3)_3$]butyl, 4-($COOCH_3$)butyl, 4-($COOC_2H_5$)butyl, 4-($COOCH_2$—$C_2H_5$)butyl, 4-[$COOCH(CH_3)_2$]butyl, 4-($COOCH_2CH_2$—$C_2H_5$)butyl, 4-(1-methylpropoxycarbonyl)butyl, 4-(2- methylpropoxycarbonyl)butyl, 4-[COOC(CH$_3$)$_3$]butyl, 4-[COO(CH$_2$)$_3$—C$_2$H$_5$]butyl, 4-[COO(CH$_2$)$_4$—C$_2$H$_5$] butyl, 5-(COOCH$_3$)pentyl, 5-(COOC$_2$H$_5$)pentyl, 5-(COOCH$_2$—C$_2$H$_5$)pentyl, 5-[COOCH(CH$_3$)$_2$] pentyl, 5-(COOCH$_2$CH$_2$—C$_2$H$_5$)pentyl, 5-(1-methylpropoxycarbonyl)pentyl, 5-(2-methylpropoxycarbonyl)pentyl, 5-[COOC(CH$_3$)$_3$] pentyl, 5-[COO(CH$_2$)$_3$—C$_2$H$_5$]pentyl, 5-[COO(CH$_2$)$_4$—C$_2$H$_5$]pentyl, 6-(COOCH$_3$)hexyl, 6-(COOC$_2$H$_5$) hexyl, 6-(COOCH$_2$—C$_2$H$_5$)hexyl, 6-[COOCH(CH$_3$)$_2$] hexyl, 6-(COOCH$_2$CH$_2$—C$_2$H$_5$)hexyl, 6-(1-methylpropoxycarbonyl)hexyl, 6-(2-methylpropoxycarbonyl)hexyl, 6-[COOC(CH$_3$)$_3$] hexyl, 6-[COO(CH$_2$)$_3$—C$_2$H$_5$]hexyl or 6-[COO(CH$_2$)$_4$—C$_2$H$_5$]hexyl, in particular CH$_2$COOCH$_3$, CH$_2$COOCH(CH$_3$)$_2$ or CH(CH$_3$)COOCH$_3$;

(C$_1$–C$_6$-alkoxy)carbonyl-C$_1$–C$_6$-alkoxy: C$_1$–C$_6$-alkoxy which is substituted by (C$_1$–C$_6$-alkoxy)carbonyl as mentioned above, eg. OCH$_2$COOCH$_3$, OCH$_2$COOC$_2$H$_5$, OCH$_2$COOCH$_2$—C$_2$H$_5$, OCH$_2$COOCH(CH$_3$)$_2$, OCH$_2$COOCH$_2$CH$_2$—C$_2$H$_5$, (1-methylpropoxycarbonyl)methoxy, (2-methylpropoxycarbonyl)methoxy, OCH$_2$COOC(CH$_3$)$_3$, OCH$_2$COO(CH$_2$)$_3$—C$_2$H$_5$, OCH$_2$COO(CH$_2$)$_4$—C$_2$H$_5$, OCH(CH$_3$)COOCH$_3$, OCH(CH$_3$)COOC$_2$H$_5$, OCH$_2$CH$_2$COOCH$_3$, OCH$_2$CH$_2$COOC$_2$H$_5$, OCH$_2$CH$_2$COOCH$_2$—C$_2$H$_5$, OCH$_2$CH$_2$COOCH(CH$_3$)$_2$, OCH$_2$CH$_2$COOCH$_2$CH$_2$—C$_2$H$_5$, 2-(1-methylpropoxycarbonyl)ethoxy, 2-(2-methylpropoxycarbonyl)ethoxy, OCH$_2$CH$_2$COOC(CH$_3$)$_3$, OCH$_2$CH$_2$COO(CH$_2$)$_3$—C$_2$H$_5$, OCH$_2$CH$_2$COO(CH$_2$)$_4$—C$_2$H$_5$, 2-(COOCH$_3$)propoxy, 2-(COOC$_2$H$_5$)propoxy, 2-(COOCH$_2$—C$_2$H$_5$)propoxy, 2-[COOCH(CH$_3$)$_2$]propoxy, 2-(COOCH$_2$CH$_2$—C$_2$H$_5$) propoxy, 2-(1-methylpropoxycarbonyl)propoxy, 2-(2-methylpropoxycarbonyl)propoxy, 2-[COOC(CH$_3$)$_3$] propoxy, 3-(COOCH$_3$)propoxy, 3-(COOC$_2$H$_5$) propoxy, 3-(COOCH$_2$—C$_2$H$_5$)propoxy, 3-[COOCH(CH$_3$)$_2$]propoxy, 3-(COOCH$_2$CH$_2$—C$_2$H$_5$)propoxy, 3-(1-methylpropoxycarbonyl)propoxy, 3-(2-methylpropoxycarbonyl)propoxy, 3-[COOC(CH$_3$)$_3$] propoxy, 3-[COO(CH$_2$)$_3$—C$_2$H$_5$]propoxy, 3-[COO(CH$_2$)$_4$—C$_2$H$_5$]propoxy, 2-(COOCH$_3$)butoxy, 2-(COOC$_2$H$_5$)butoxy, 2-(COOCH$_2$—C$_2$H$_5$)butoxy, 2-[COOCH(CH$_3$)$_2$]butoxy, 2-(COOCH$_2$CH$_2$—C$_2$H$_5$) butoxy, 2-(1-methylpropoxycarbonyl)butoxy, 2-(2-methylpropoxycarbonyl)butoxy, 2-[COOC(CH$_3$)$_3$] butoxy, 3-(COOCH$_3$)butoxy, 3-(COOC$_2$H$_5$)butoxy, 3-(COOCH$_2$—C$_2$H$_5$)butoxy, 3-[COOCH(CH$_3$)$_2$] butoxy, 3-(COOCH$_2$CH$_2$—C$_2$H$_5$)butoxy, 3-(1-methylpropoxycarbonyl)butoxy, 3-(2-methylpropoxycarbonyl)butoxy, 3-[COOC(CH$_3$)$_3$] butoxy, 4-(COOCH$_3$)butoxy, 4-(COOC$_2$H$_5$)butoxy, 4-(COOCH$_2$—C$_2$H$_5$)butoxy, 4-[COOCH(CH$_3$)$_2$] butoxy, 4-(COOCH$_2$CH$_2$—C$_2$H$_5$)butoxy, 4-(1-methylpropoxycarbonyl)butoxy, 4-(2-methylpropoxycarbonyl)butoxy, 4-[COOC(CH$_3$)$_3$] butoxy, 4-[COO(CH$_2$)$_3$—C$_2$H$_5$]butoxy, 4-[COO(CH$_2$)$_4$—C$_2$H$_5$]butoxy, 5-(COOCH$_3$)pentoxy, 5-(COOC$_2$H$_5$)-pentoxy, 5-(COOCH$_2$—C$_2$H$_5$)pentoxy, 5-[COOCH(CH$_3$)$_2$]pentoxy, 5-(COOCH$_2$CH$_2$—C$_2$H$_5$) pentoxy, 5-(1-methylpropoxycarbonyl)pentoxy, 5-(2-methylpropoxycarbonyl)pentoxy, 5-[COOC(CH$_3$)$_3$] pentoxy, 5-[COO(CH$_2$)$_3$—C$_2$H$_5$]pentoxy, 5-[COO(CH$_2$)$_4$—C$_2$H$_5$]pentoxy, 6-(COOCH$_3$)hexyloxy, 6-(COOC$_2$H$_5$)hexyloxy, 6-(COOCH$_2$—C$_2$H$_5$) hexyloxy, 6-[COOCH(CH$_3$)$_2$]hexyloxy, 6-(COOCH$_2$CH$_2$—C$_2$H$_5$)hexyloxy, 6-(1-methylpropoxycarbonyl)hexyloxy, 6-(2-methylpropoxycarbonyl)hexyloxy, 6-[COOC(CH$_3$)$_3$] hexyloxy, 6-[COO(CH$_2$)$_3$—C$_2$H$_5$]hexyloxy or 6-[COO(CH$_2$)$_4$—C$_2$H$_5$]hexyloxy, in particular OCH$_2$COOCH$_3$, OCH$_2$COOCH(CH$_3$)$_2$, OCH(CH$_3$) COOCH$_3$ or OCH$_2$CH$_2$COOCH$_3$;

C$_1$–C$_6$-alkylthio: eg. SCH$_3$, SC$_2$H$_5$, n-propylthio, SCH(CH$_3$)$_2$, n-butylthio, 1-methylpropylthio, 2-methylpropylthio, SC(CH$_3$)$_3$, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, in particular SCH$_3$ or SC$_2$H$_5$;

C$_1$–C$_6$-haloalkylthio: a C$_1$–C$_6$-alkylthio radical as mentioned above which is partially or fully substituted by fluorine, chlorine, bromine and/or iodine, eg. SCH$_2$F, SCHF$_2$, SCF$_3$, SCH$_2$Cl, SCH(Cl)$_2$, SC(Cl)$_3$, SCHFCl, SCF(Cl)$_2$, SCF$_2$Cl, SCF$_2$Br, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, SC$_2$F$_5$, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(CH$_2$F)-2-fluoroethylthio, 1-(CH$_2$Cl)-2-chloroethylthio, 1-(CH$_2$Br)-2-bromoethylthio, 4-fluorobutylthio, 4-chlorobutylthio, 4-bromobutylthio, 5-fluoropentylthio, 5-chloropentylthio, 5-bromopentoxy, 5-iodopentoxy, undecafluoropentoxy, 6-fluorohexylthio or 6-chlorohexylthio, in particular SCHF$_2$, SCF$_3$ or SC(Cl)$_3$;

C$_1$–C$_6$-alkylsulfinyl: eg. SOCH$_3$, SOC$_2$H$_5$, n-propylsulfinyl, SOCH(CH$_3$)$_2$, n-butylsulfinyl, 1-methylpropylsulfinyl, 2-methylpropylsulfinyl, SOC(CH$_3$)$_3$, n-pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, n-hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl, in particular SOCH$_3$ or SOC$_2$H$_5$;

C$_1$–C$_6$-alkylsulfonyl: eg. SO$_2$CH$_3$, SO$_2$C$_2$H$_5$, n-propylsulfonyl, SO$_2$CH(CH$_3$)$_2$, n-butylsulfonyl, 1-methylpropylsulfonyl, 2-methylpropylsulfonyl, SO$_2$C(CH$_3$)$_3$, n-pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, n-hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular SO$_2$CH$_3$ or SO$_2$C$_2$H$_5$;

C$_1$–C$_6$-alkylaminosulfonyl: eg. H$_3$C—NHSO$_2$—, H$_5$C$_2$—NHSO$_2$—, n-propyl-NHSO$_2$—, (CH$_3$)$_2$CH—NHSO$_2$—, n-butyl-NHSO$_2$—, 1-methylpropyl-NHSO$_2$—, 2-methylpropyl-NHSO$_2$—, (CH$_3$)$_3$C—NHSO$_2$—, n-pentyl-NHSO$_2$—, 1-methylbutyl-NHSO$_2$—, 2-methylbutyl-NHSO$_2$—, 3-methylbutyl-NHSO$_2$—, 2,2-dimethylpropyl-NHSO$_2$—, 1-ethylpropyl-NHSO$_2$—, n-hexyl-NHSO$_2$—, 1,1-dimethylpropyl-NHSO$_2$—, 1,2-dimethylpropyl-NHSO$_2$—, 1-methylpentyl-NHSO$_2$—, 2-methylpentyl-NHSO$_2$—, 3-methylpentyl-NHSO$_2$—, 4-methylpentyl-NHSO$_2$—, 1,1-dimethylbutyl-NHSO$_2$—, 1,2-dimethylbutyl-NHSO$_2$—, 1,3-dimethylbutyl-NHSO$_2$—, 2,2-dimethylbutyl-NHSO$_2$—, 2,3-dimethylbutyl-NHSO$_2$—, 3,3-dimethylbutyl-NHSO$_2$—, 1-ethylbutyl-NHSO$_2$—, 2-ethylbutyl-NHSO$_2$—, 1,1,2-trimethylpropyl-NHSO$_2$—, 1,2,2-trimethylpropyl-NHSO$_2$—, 1-ethyl-1-methylpropyl-NHSO$_2$— or 1-ethyl-2-methylpropyl-NHSO$_2$—, in particular H$_3$C—NHSO$_2$— or H$_5$C$_2$—NHSO$_2$—;

di-(C$_1$–C$_6$-alkyl)aminosulfonyl: eg. (CH$_3$)$_2$N—SO$_2$—, (C$_2$H$_5$)$_2$N—SO$_2$—, N,N-dipropylamino-SO$_2$—, N,N-di(1-methylethyl)amino-SO$_2$—, N,N-dibutylamino-SO$_2$—, N,N-di(1-methylpropyl)amino-SO$_2$—, N,N-di(2-methylpropyl)amino-SO$_2$—, N,N-di(1,1-dimethylethyl)amino-SO$_2$—, N-ethyl-N-methylamino-SO$_2$—, N-methyl-N-propylamino-SO$_2$—, N-methyl-N-(1-methylethyl)amino-SO$_2$—, N-butyl-N-methylamino-SO$_2$—, N-methyl-N-(1-methylpropyl)amino-SO$_2$—, N-methyl-N-(2-methylpropyl)amino-SO$_2$—, N-(1,1-dimethylethyl)-N-methylamino-SO$_2$—, N-ethyl-N-propylamino-SO$_2$—, N-ethyl-N-(1-methylethyl)amino-SO$_2$—, N-butyl-N-ethylamino-SO$_2$—, N-ethyl-N-(1-methylpropyl)amino-SO$_2$—, N-ethyl-N-(2-methylpropyl)amino-SO$_2$—, N-ethyl-N-(1,1-dimethylethyl)amino-SO$_2$—, N-(1-methylethyl)-N-propylamino-SO$_2$—, N-butyl-N-propylamino-SO$_2$—, N-(1-methylpropyl)-N-propylamino-SO$_2$—, N-(2-methylpropyl)-N-propylamino-SO$_2$—, N-(1,1-dimethylethyl)-N-propylamino-SO$_2$—, N-butyl-N-(1-methylethyl)amino-SO$_2$—, N-(1-methylethyl)-N-(1-methylpropyl)amino-SO$_2$—, N-(1-methylethyl)-N-(2-methylpropyl)-amino-SO$_2$—, N-(1,1-dimethylethyl)-N-(1-methylethyl)amino-SO$_2$—, N-butyl-N-(1-methylpropyl)amino-SO$_2$—, N-butyl-N-(2-methylpropyl)amino-SO$_2$—, N-butyl-N-(1,1-dimethylethyl)amino-SO$_2$—, N-(1-methylpropyl)-N-(2-methylpropyl)amino-SO$_2$—, N-(1,1-dimethylethyl)-N-(1-methylpropyl)amino-SO$_2$— or N-(1,1-dimethylethyl)-N-(2-methylpropyl)amino-SO$_2$—, in particular (CH$_3$)$_2$N—SO$_2$—, (C$_2$H$_5$)$_2$N—SO$_2$— or N-ethyl-N-methylamino-SO$_2$—;

C$_3$–C$_6$-alkenyl: eg. prop-1-en-1-yl, allyl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-2-en-1-yl, 1,2-dimethylbut-3-en-1-yl, 1,3-dimethylbut-2-en-1-yl, 1,3-dimethylbut-2-en-1-yl, 1,3-dimethylbut-3-en-1-yl, 2,2-dimethylbut-3-en-1-yl, 2,3-dimethylbut-3-en-1-yl, 2,3-dimethylbut-2-en-1-yl, 2,3-dimethylbut-3-en-1-yl, 3,3-dimethylbut-2-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-2-en-1-yl, 2-ethylbut-2-en-1-yl, 2-ethylbut-3-en-1-yl, 1,1,2-trimethyl-prop-2-en-1-yl, 1-ethyl-1-methylprop-2-en-1-yl, 1-ethyl-2-methylprop-2-en-1-yl or 1-ethyl-2-methylprop-2-en-1-yl, in particular allyl;

C$_3$–C$_6$-alkynyl: eg. prop-1-yn-1-yl, propargyl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methyl-pent-1-yn-1-yl, 4-methyl-pent-2-yn-4-yl or 4-methylpent-2-yn-5-yl, in particular propargyl;

C$_3$–C$_6$-alkenyloxy: eg. prop-1-en-1-yloxy, allyloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent- 3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-2-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-3-en-1-yloxy, 2,3-dimethylbut-2-en-1-yloxy, 2,3-dimethylbut-3-en-1-yloxy, 3,3-dimethylbut-2-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-2-en-1-yloxy, 2-ethylbut-2-en-1-yloxy, 2-ethylbut-3-en-1-yloxy, 1,1,2-trimethyl-prop-2-en-1-yloxy, 1-ethyl-1-methylprop-2-en-1-yloxy, 1-ethyl-2-methyl-prop-1-en-1-yloxy or 1-ethyl-2-methylprop-2-en-1-yloxy, in particular allyloxy;

$C_3$–$C_6$-alkynyloxy: eg. prop-1-yn-1-yloxy, propargyloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methyl-but-1-yn-3-yloxy, 3-methyl-but-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy, in particular propargyloxy.

With a view to the use of the substituted 2-phenylpyridines I as herbicides and/or compounds which have a desiccant/defoliant action, the variables preferably have the following meanings, to be precise in each case alone or in combination:

n is zero;

$R^1$ is $C_1$–$C_6$-alkylsulfonyl, in particular $SO_2CH_3$;

$R^2$ is halogen, in particular chlorine;

$R^3$ is hydrogen, fluorine or chlorine, especially preferably fluorine or chorine, in particular fluorine;

$R^4$ is cyano or halogen, especially preferably cyano or chlorine, in particular chlorine;

$R^5$ is hydrogen, nitro, cyano, hydroxylamino, $C_1$–$C_6$-alkyl (in particular $CH_3$), $C_1$–$C_6$-haloalkyl (in particular halomethyl), —COCl, —CO—$OR^6$, —CO—O—($C_1$–$C_4$-alkylene)—CO—$OR^6$, —O—($C_1$–$C_4$-alkylene)—CO—$OR^6$, —O—($C_1$–$C_4$-alkylene)—CO—O—($C_1$–$C_4$-alkylene)—CO—$OR^6$, —$OR^9$, formyl, —CH=N—$OR^{15}$ or —$NH_2$;

$R^6$ is hydrogen, $C_1$–$C_6$-alkyl, $C_3$–$C_6$-alkenyl, $C_3$–$C_6$-alkynyl or $C_1$–$C_6$-alkoxy-$C_1$–$C_6$-alkyl;

$R^9$ is hydrogen, $C_1$–$C_6$-alkyl, $C_3$–$C_6$-alkenyl or $C_3$–$C_6$-alkynyl;

$R^{15}$ is $C_1$–$C_6$-alkyl.

Very especially preferred are the compounds of the formula Ia (=I where n=zero; $R^1$=methylsulfonyl; $R^2$ and $R^4$=chlorine; $R^3$=fluorine), in particular the compounds of Table 1:

TABLE 1

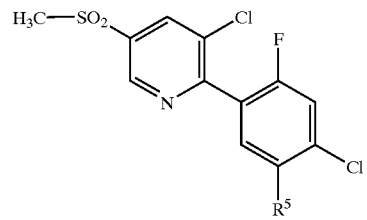

Ia

| No. | $R^5$ |
|---|---|
| Ia.1 | —H |
| Ia.2 | —F |
| Ia.3 | —Cl |
| Ia.4 | —Br |
| Ia.5 | —I |
| Ia.6 | —CN |
| Ia.7 | —$CH_3$ |
| Ia.8 | —$CH_2Cl$ |
| Ia.9 | —$CHCl_2$ |
| Ia.10 | —$CCl_3$ |
| Ia.11 | —$CH_2Br$ |
| Ia.12 | —$CHBr_2$ |
| Ia.13 | —COCl |
| Ia.14 | —CO—OH |
| Ia.15 | —CO—$OCH_3$ |
| Ia.16 | —CO—$OC_2H_5$ |
| Ia.17 | —CO—$OCH_2$—$C_2H_5$ |
| Ia.18 | —CO—$OCH(CH_3)_2$ |
| Ia.19 | —CO—$OCH_2$—$CH_2$—$C_2H_5$ |
| Ia.20 | —CO—$OCH_2$—$CH(CH_3)_2$ |
| Ia.21 | —CO—$OCH_2$—$CH_2$—$CH_2$—$C_2H_5$ |
| Ia.22 | —CO—$OCH_2$—$CCl_3$ |

TABLE 1-continued

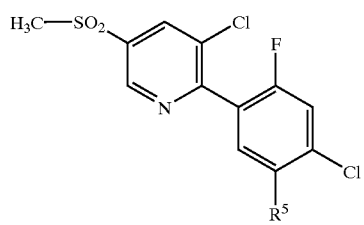

Ia

| No. | R$^5$ |
|---|---|
| Ia.23 | —CO—OCH$_2$—CF$_3$ |
| Ia.24 | —CO—OCH$_2$—CH=CH$_2$ |
| Ia.25 | —CO—OCH$_2$—CH=CH—CH$_3$ |
| Ia.26 | —CO—OCH$_2$—CH$_2$—CH=CH$_2$ |
| Ia.27 | —CO—OCH(CH$_3$)—CH=CH$_2$ |
| Ia.28 | —CO—OCH$_2$—CH$_2$—CH$_2$—CH=CH$_2$ |
| Ia.29 | —CO—OCH$_2$—CH=C(CH$_3$)$_2$ |
| Ia.30 | —CO—OCH$_2$—C(CH$_3$)=CH—CH$_3$ |
| Ia.31 | —CO—OCH$_2$—C≡CH |
| Ia.32 | —CO—OCH(CH$_3$)—C≡CH |
| Ia.33 | —CO—OCH$_2$—C≡C—CH$_3$ |
| Ia.34 | —CO—OCH$_2$—C≡C—C$_2$H$_5$ |
| Ia.35 | —CO—O-cyclopropyl |
| Ia.36 | —CO—O-cyclobutyl |
| Ia.37 | —CO—O-cyclopentyl |
| Ia.38 | —CO—O-cyclohexyl |
| Ia.39 | —CO—OCH$_2$—CH$_2$—OCH$_3$ |
| Ia.40 | —CO—OCH$_2$—CH$_2$—OC$_2$H$_5$ |
| Ia.41 | —CO—OCH$_2$—CH$_2$—OCH$_2$—CH$_2$—CH$_3$ |
| Ia.42 | —CO—OCH$_2$—CH$_2$—OCH(CH$_3$)$_2$ |
| Ia.43 | —CO—O-(oxetan-3-yl) |
| Ia.44 | —CO—NH$_2$ |
| Ia.45 | —CO—NH—CH$_3$ |
| Ia.46 | —CO—N(CH$_3$)$_2$ |
| Ia.47 | —CO—NH—CH$_2$—CO—OH |
| Ia.48 | —CO—NH—CH$_2$—CO—OCH$_3$ |
| Ia.49 | —CO—NH—CH$_2$—CO—OC$_2$H$_5$ |
| Ia.50 | —CO—NH—CH$_2$—CO—OCH$_2$—C$_2$H$_5$ |
| Ia.51 | —CO—NH—CH$_2$—CO—OCH$_2$—CH$_2$—C$_2$H$_5$ |
| Ia.52 | —CO—NH—CH(CH$_3$)—CO—OH |
| Ia.53 | —CO—NH—CH(CH$_3$)—CO—OCH$_3$ |
| Ia.54 | —CO—NH—CH(CH$_3$)—CO—OC$_2$H$_5$ |
| Ia.55 | —CO—NH—CH(CH$_3$)—CO—OCH$_2$—C$_2$H$_5$ |
| Ia.56 | —CO—NH—CH(CH$_3$)—CO—OCH$_2$—CH$_2$—C$_2$H$_5$ |
| Ia.57 | —CO—N(CH$_3$)—CH$_2$—CO—OH |
| Ia.58 | —CO—N(CH$_3$)—CH$_2$—CO—OCH$_3$ |
| Ia.59 | —CO—N(CH$_3$)—CH$_2$—CO—OC$_2$H$_5$ |
| Ia.60 | —CO—N(CH$_3$)—CH$_2$—CO—OCH$_2$—C$_2$H$_5$ |
| Ia.61 | —CO—N(CH$_3$)—CH$_2$—CO—OCH$_2$—CH$_2$—C$_2$H$_5$ |
| Ia.62 | —CO—N(CH$_3$)—CH(CH$_3$)—CO—OH |
| Ia.63 | —CO—N(CH$_3$)—CH(CH$_3$)—CO—OCH$_3$ |
| Ia.64 | —CO—N(CH$_3$)—CH(CH$_3$)—CO—OC$_2$H$_5$ |
| Ia.65 | —CO—N(CH$_3$)—CH(CH$_3$)—CO—OCH$_2$—C$_2$H$_5$ |
| Ia.66 | —CO—N(CH$_3$)—CH(CH$_3$)—CO—OCH$_2$—CH$_2$—C$_2$H$_5$ |
| Ia.67 | —CO-pyrrolidin-1-yl |
| Ia.68 | —CO-piperidin-1-yl |
| Ia.69 | —CO-[2-(COOCH$_3$)-pyrrolidin-1-yl] |
| Ia.70 | —CO-[2-(COOC$_2$H$_5$)-pyrrolidin-1-yl] |
| Ia.71 | —CO—OCH$_2$—CO—OH |
| Ia.72 | —CO—OCH$_2$—CO—OCH$_3$ |
| Ia.73 | —CO—OCH$_2$—CO—OC$_2$H$_5$ |
| Ia.74 | —CO—OCH$_2$—CO—OCH$_2$—C$_2$H$_5$ |
| Ia.75 | —CO—OCH$_2$—CO—OCH(CH$_3$)$_2$ |
| Ia.76 | —CO—OCH$_2$—CO—OCH$_2$—CH$_2$—C$_2$H$_5$ |
| Ia.77 | —CO—OCH$_2$—CO—OCH$_2$—CH$_2$—CH(CH$_3$)$_2$ |
| Ia.78 | —CO—OCH$_2$—CO—OCH(CH$_3$)—C$_2$H$_5$ |
| Ia.79 | —CO—OCH$_2$—CO—OC(CH$_3$)$_3$ |
| Ia.80 | —CO—OCH$_2$—CO—OCH$_2$—CH$_2$—CH$_2$—C$_2$H$_5$ |
| Ia.81 | —CO—OCH$_2$—CO—OCH$_2$—CH$_2$—CH(CH$_3$)$_2$ |
| Ia.82 | —CO—OCH(CH$_3$)—CO—OH |
| Ia.83 | —CO—OCH(CH$_3$)—CO—OCH$_3$ |
| Ia.84 | —CO—OCH(CH$_3$)—CO—OC$_2$H$_5$ |
| Ia.85 | —CO—OCH(CH$_3$)—CO—OCH$_2$—C$_2$H$_5$ |
| Ia.86 | —CO—OCH(CH$_3$)—CO—OCH(CH$_3$)$_2$ |

TABLE 1-continued

Ia

Structure: A pyridine ring with H₃C—SO₂ group at the 5-position, Cl at the 3-position, connected at the 2-position to a phenyl ring bearing F (ortho), Cl (para to F), and R⁵.

| No. | R⁵ |
|---|---|
| Ia.87 | —CO—OCH(CH₃)—CO—OCH₂—CH₂—C₂H₅ |
| Ia.88 | —CO—OCH(CH₃)—CO—OCH₂—CH(CH₃)₂ |
| Ia.89 | —CO—OCH(CH₃)—CO—OCH(CH₃)—C₂H₅ |
| Ia.90 | —CO—OCH(CH₃)—CO—OC(CH₃)₃ |
| Ia.91 | —CO—OCH(CH₃)—CO—OCH₂—CH₂—CH₂—C₂H₅ |
| Ia.92 | —CO—OCH(CH₃)—CO—OCH₂—CH₂—CH(CH₃)₂ |
| Ia.93 | —CO—OCH₂—CO—NH₂ |
| Ia.94 | —CO—OCH₂—CO—NH—CH₃ |
| Ia.95 | —CO—OCH₂—CO—N(CH₃)₂ |
| Ia.96 | —CO—OCH₂—CO—N(CH₃)—CH₂—CO—OH |
| Ia.97 | —CO—OCH₂—CO—N(CH₃)—CH₂—CO—OCH₃ |
| Ia.98 | —CO—OCH₂—CO—N(CH₃)—CH₂—CO—OC₂H₅ |
| Ia.99 | —CO—OCH₂—CO-pyrrolidin-1-yl |
| Ia.100 | —CO—OCH₂—CO-piperidin-1-yl |
| Ia.101 | —CO—OCH₂—CO-[2-(COOCH₃)-pyrrolidin-1-yl] |
| Ia.102 | —CO—OCH₂—CO-[2-(COOC₂H₅)-pyrrolidin-1-yl] |
| Ia.103 | —CO—OCH(CH₃)—CO—NH₂ |
| Ia.104 | —CO—OCH(CH₃)—CO—NH—CH₃ |
| Ia.105 | —CO—OCH(CH₃)—CO—N(CH₃)₂ |
| Ia.106 | —CO—OCH(CH₃)—CO—N(CH₃)—CH₂—CO—OH |
| Ia.107 | —CO—OCH(CH₃)—CO—N(CH₃)—CH₂—CO—OCH₃ |
| Ia.108 | —CO—OCH(CH₃)—CO—N(CH₃)—CH₂—CO—OC₂H₅ |
| Ia.109 | —CO—OCH(CH₃)—CO-pyrrolidin-1-yl |
| Ia.110 | —CO—OCH(CH₃)—CO-piperidin-1-yl |
| Ia.111 | —CO—OCH(CH₃)—CO-[2-(COOCH₃)-pyrrolidin-1-yl] |
| Ia.112 | —CO—OCH(CH₃)—CO-[2-(COOC₂H₅)-pyrrolidin-1-yl] |
| Ia.113 | —OCH₂—CHO |
| Ia.114 | —OCH₂—CO—CH₃ |
| Ia.115 | —OCH₂—CO—C₂H₅ |
| Ia.116 | —OCH₂—CO—CH(CH₃)₂ |
| Ia.117 | —OCH₂—CO—CH₂—C₂H₅ |
| Ia.118 | —OCH₂—CO—CH₂—CH₂—C₂H₅ |
| Ia.119 | —OCH₂—CO—CH₂—CH(CH₃)₂ |
| Ia.120 | —OCH₂—CO—CH(CH₃)—C₂H₅ |
| Ia.121 | —OCH₂—CO—C(CH₃)₃ |
| Ia.122 | —OCH(CH₃)—CO—CH₃ |
| Ia.123 | —OCH(CH₃)—CO—C₂H₅ |
| Ia.124 | —OCH(CH₃)—CO—CH₂—C₂H₅ |
| Ia.125 | —OCH(CH₃)—CO—CH(CH₃)₂ |
| Ia.126 | —OCH(CH₃)—CO—CH₂—CH₂—C₂H₅ |
| Ia.127 | —OCH(CH₃)—CO—CH₂—CH(CH₃)₂ |
| Ia.128 | —OCH(CH₃)—CO—CH(CH₃)—C₂H₅ |
| Ia.129 | —OCH(CH₃)—CO—C(CH₃)₃ |
| Ia.130 | —OCH₂—CO—CH₂—Cl |
| Ia.131 | —OCH(CH₃)—CO—CH₂—Cl |
| Ia.132 | —OCH₂—CO—CH₂—CH=CH₂ |
| Ia.133 | —OCH(CH₃)—CO—CH₂—CH=CH₂ |
| Ia.134 | —OCH₂—CO—CH₂—C≡CH |
| Ia.135 | —OCH(CH₃)—CO—CH₂—C≡CH |
| Ia.136 | —OCH₂—CO-cyclopentyl |
| Ia.137 | —OCH(CH₃)—CO-cyclohexyl |
| Ia.138 | —OCH₂—CO—CH₂—OCH₃ |
| Ia.139 | —OCH(CH₃)—CO—CH₂—OCH₃ |
| Ia.140 | —OCH₂—CO—CH₂—OC₂H₅ |
| Ia.141 | —OCH(CH₃)—CO—CH₂—OC₂H₅ |
| Ia.142 | —OCH₂—CO—CH₂—CH₂—OCH₃ |
| Ia.143 | —OCH(CH₃)—CO—CH₂—CH₂—OCH₃ |
| Ia.144 | —OCH₂—CO—CH₂—CH₂—OC₂H₅ |
| Ia.145 | —OCH(CH₃)—CO—CH₂—CH₂—OC₂H₅ |
| Ia.146 | —SCH₂—CHO |
| Ia.147 | —SCH₂—CO—CH₃ |
| Ia.148 | —SCH₂—CO—C₂H₅ |
| Ia.149 | —SCH₂—CO—CH(CH₃)₂ |
| Ia.150 | —SCH₂—CO—CH₂—C₂H₅ |

TABLE 1-continued

Ia

[Structure: pyridine with H3C—SO2 group, Cl, connected to phenyl ring with F, Cl, and R5 substituents]

| No. | R⁵ |
|---|---|
| Ia.151 | —SCH(CH₃)—CO—CH₂—CH₂—C₂H₅ |
| Ia.152 | —SCH(CH₃)—CO—CH₂—CH(CH₃)₂ |
| Ia.153 | —SCH(CH₃)—CO—CH(CH₃)—C₂H₅ |
| Ia.154 | —SCH(CH₃)—CO—C(CH₃)₃ |
| Ia.155 | —SCH₂—CO—CH₂—CH=CH₂ |
| Ia.156 | —SCH(CH₃)—CO—CH₂—CH=CH₂ |
| Ia.157 | —SCH₂—CO—CH₂—CH≡CH |
| Ia.158 | —SCH(CH₃)—CO—CH₂—CH≡CH |
| Ia.159 | —SCH₂—CO-cyclopentyl |
| Ia.160 | —SCH(CH₃)—CO-cyclopentyl |
| Ia.161 | —SCH₂—CO-cyclohexyl |
| Ia.162 | —SCH(CH₃)—CO-cyclohexyl |
| Ia.163 | —SCH₂—CO—CH₂—OCH₃ |
| Ia.164 | —SCH(CH₃)—CO—CH₂—OCH₃ |
| Ia.165 | —SCH₂—CO—CH₂—OC₂H₅ |
| Ia.166 | —SCH(CH₃)—CO—CH₂—OC₂H₅ |
| Ia.167 | —SCH₂—CO—CH₂—CH₂—OCH₃ |
| Ia.168 | —SCH(CH₃)—CO—CH₂—CH₂—OCH₃ |
| Ia.169 | —SCH₂—CO—CH₂—CH₂—OC₂H₅ |
| Ia.170 | —SCH(CH₃)—CO—CH₂—CH₂—OC₂H₅ |
| Ia.171 | —OCH₂—CO—OH |
| Ia.172 | —OCH₂—CO—OCH₃ |
| Ia.173 | —OCH₂—CO—OC₂H₅ |
| Ia.174 | —OCH₂—CO—OCH₂—C₂H₅ |
| Ia.175 | —OCH₂—CO—OCH(CH₃)₂ |
| Ia.176 | —OCH₂—CO—OCH₂—CH₂—C₂H₅ |
| Ia.177 | —OCH₂—CO—OCH₂—CH(CH₃)₂ |
| Ia.178 | —OCH₂—CO—OC(CH₃)₃ |
| Ia.179 | —OCH₂—CO—OCH₂—CH₂—CH₂—C₂H₅ |
| Ia.180 | —OCH₂—CO—OCH₂—CH₂—CH(CH₃)₂ |
| Ia.181 | —OCH(CH₃)—CO—OH |
| Ia.182 | —OCH(CH₃)—CO—OCH₃ |
| Ia.183 | —OCH(CH₃)—CO—OC₂H₅ |
| Ia.184 | —OCH(CH₃)—CO—OCH₂—OC₂H₅ |
| Ia.185 | —OCH(CH₃)—CO—OCH(CH₃)₂ |
| Ia.186 | —OCH(CH₃)—CO—OCH₂—CH₂—C₂H₅ |
| Ia.187 | —OCH(CH₃)—CO—OCH₂—CH(CH₃)₂ |
| Ia.188 | —OCH(CH₃)—CO—OC(CH₃)₃ |
| Ia.189 | —OCH(CH₃)—CO—OCH₂—CH₂—CH₂—C₂H₅ |
| Ia.190 | —OCH(CH₃)—CO—OCH₂—CH₂—CH(CH₃)₂ |
| Ia.191 | —SCH₂—CO—OH |
| Ia.192 | —SCH₂—CO—OCH₃ |
| Ia.193 | —SCH₂—CO—OC₂H₅ |
| Ia.194 | —SCH₂—CO—OCH₂—C₂H₅ |
| Ia.195 | —SCH₂—CO—OCH(CH₃)₂ |
| Ia.196 | —SCH₂—CO—OCH₂—CH₂—C₂H₅ |
| Ia.197 | —SCH₂—CO—OCH₂—CH(CH₃)₂ |
| Ia.198 | —SCH₂—CO—OC(CH₃)₃ |
| Ia.199 | —SCH₂—CO—OCH₂—CH₂—CH₂—C₂H₅ |
| Ia.200 | —SCH₂—CO—OCH₂—CH₂—CH(CH₃)₂ |
| Ia.201 | —SCH(CH₃)—CO—OH |
| Ia.202 | —SCH(CH₃)—CO—OCH₃ |
| Ia.203 | —SCH(CH₃)—CO—OC₂H₅ |
| Ia.204 | —SCH(CH₃)—CO—OCH₂—C₂H₅ |
| Ia.205 | —SCH(CH₃)—CO—OCH(CH₃)₂ |
| Ia.206 | —SCH(CH₃)—CO—OCH₂—CH₂—C₂H₅ |
| Ia.207 | —SCH(CH₃)—CO—OCH₂—CH(CH₃)₂ |
| Ia.208 | —SCH(CH₃)—CO—OC(CH₃)₃ |
| Ia.209 | —SCH(CH₃)—CO—OCH₂—CH₂—CH₂—C₂H₅ |
| Ia.210 | —SCH(CH₃)—CO—OCH₂—CH₂—CH(CH₃)₂ |
| Ia.211 | —OCH₂—CO—OCH₂—CO—OH |
| Ia.212 | —OCH₂—CO—OCH₂—CO—OCH₃ |
| Ia.213 | —OCH₂—CO—OCH₂—CO—OC₂H₅ |
| Ia.214 | —OCH₂—CO—OCH₂—CO—OCH₂—C₂H₅ |

TABLE 1-continued

Ia

[Structure: pyridine with H₃C—SO₂ at 5-position, Cl at 3-position, connected at 2-position to phenyl ring bearing F (ortho), Cl (para), and R⁵ (meta to connection)]

| No. | R⁵ |
|---|---|
| Ia.215 | —OCH₂—CO—OCH₂—CO—OCH(CH₃)₂ |
| Ia.216 | —OCH₂—CO—OCH₂—CO—OCH₂—CH₂—C₂H₅ |
| Ia.217 | —OCH₂—CO—OCH₂—CO—OCH₂—CH(CH₃)₂ |
| Ia.218 | —OCH₂—CO—OCH₂—CO—OCH(CH₃)—C₂H₅ |
| Ia.219 | —OCH₂—CO—OCH₂—CO—OC(CH₃)₃ |
| Ia.220 | —OCH₂—CO—OCH(CH₃)—CO—OH |
| Ia.221 | —OCH₂—CO₂—CH(CH₃)—CO—OCH₃ |
| Ia.222 | —OCH₂—CO—OCH(CH₃)—CO—OC₂H₅ |
| Ia.223 | —OCH₂—CO—OCH(CH₃)—CO—OCH₂—C₂H₅ |
| Ia.224 | —OCH₂—CO—OCH(CH₃)—CO—OCH(CH₃)₂ |
| Ia.225 | —OCH₂—CO—OCH(CH₃)—CO—OCH₂—CH₂—C₂H₅ |
| Ia.226 | —OCH₂—CO—OCH(CH₃)—CO—OCH₂—CH(CH₃)₂ |
| Ia.227 | —OCH₂—CO—OCH(CH₃)—CO—OCH(CH₃)—C₂H₅ |
| Ia.228 | —OCH₂—CO—OCH(CH₃)—CO—OC(CH₃)₃ |
| Ia.229 | —OCH(CH₃)—CO—OCH₂—CO—OH |
| Ia.230 | —OCH(CH₃)—CO—OCH₂—CO—OCH₃ |
| Ia.231 | —OCH(CH₃)—CO—OCH₂—CO—OC₂H₅ |
| Ia.232 | —OCH(CH₃)—CO—OCH₂—CO—OCH₂—C₂H₅ |
| Ia.233 | —OCH(CH₃)—CO—OCH₂—CO—OCH(CH₃)₂ |
| Ia.234 | —OCH(CH₃)—CO—OCH₂—CO—OCH₂—CH₂—C₂H₅ |
| Ia.235 | —OCH(CH₃)—CO—OCH₂—CO—OCH₂—CH(CH₃)₂ |
| Ia.236 | —OCH(CH₃)—CO—OCH₂—CO—OCH(CH₃)—C₂H₅ |
| Ia.237 | —OCH(CH₃)—CO—OCH₂—CO—OC(CH₃)₃ |
| Ia.238 | —OCH(CH₃)—CO—OCH(CH₃)—CO—OH |
| Ia.239 | —OCH(CH₃)—CO—OCH(CH₃)—CO—OCH₃ |
| Ia.240 | —OCH(CH₃)—CO—OCH(CH₃)—CO—OC₂H₅ |
| Ia.241 | —OCH(CH₃)—CO—OCH(CH₃)—CO—OCH₂—C₂H₅ |
| Ia.242 | —OCH(CH₃)—CO—OCH(CH₃)—CO—OCH(CH₃)₂ |
| Ia.243 | —OCH(CH₃)—CO—OCH(CH₃)—CO—OCH₂—CH₂—C₂H₅ |
| Ia.244 | —OCH(CH₃)—CO—OCH(CH₃)—CO—OCH₂—CH(CH₃)₂ |
| Ia.245 | —OCH(CH₃)—CO—OCH(CH₃)—CO—OCH(CH₃)—C₂H₅ |
| Ia.246 | —OCH(CH₃)—CO—OCH(CH₃)—CO—OC(CH₃)₃ |
| Ia.247 | —SCH₂—CO—OCH₂—CO—OH |
| Ia.248 | —SCH₂—CO—OCH₂—CO—OCH₃ |
| Ia.249 | —SCH₂—CO—OCH₂—CO—OC₂H₅ |
| Ia.250 | —SCH₂—CO—OCH₂—CO—OCH₂—C₂H₅ |
| Ia.251 | —SCH₂—CO—OCH₂—CO—OCH(CH₃)₂ |
| Ia.252 | —SCH₂—CO—OCH₂—CO—OCH₂—CH₂—C₂H₅ |
| Ia.253 | —SCH₂—CO—OCH₂—CO—OCH₂—CH(CH₃)₂ |
| Ia.254 | —SCH₂—CO—OCH₂—CO—OCH(CH₃)—C₂H₅ |
| Ia.255 | —SCH₂—CO—OCH₂—CO—OC(CH₃)₃ |
| Ia.256 | —SCH₂—CO—OCH(CH₃)—CO—OH |
| Ia.257 | —SCH₂—CO—OCH(CH₃)—CO—OCH₃ |
| Ia.258 | —SCH₂—CO—OCH(CH₃)—CO—OC₂H₅ |
| Ia.259 | —SCH₂—CO—OCH(CH₃)—CO—OCH₂—C₂H₅ |
| Ia.260 | —SCH₂—CO—OCH(CH₃)—CO—OCH(CH₃)₂ |
| Ia.261 | —SCH₂—CO—OCH(CH₃)—CO—OCH₂—CH₂—C₂H₅ |
| Ia.262 | —SCH₂—CO—OCH(CH₃)—CO—OCH₂—CH(CH₃)₂ |
| Ia.263 | —SCH₂—CO—OCH(CH₃)—CO—OCH(CH₃)—C₂H₅ |
| Ia.264 | —SCH₂—CO—OCH(CH₃)—CO—OC(CH₃)₃ |
| Ia.265 | —SCH(CH₃)—CO—OCH₂—CO—OH |
| Ia.266 | —SCH(CH₃)—CO—OCH₂—CO—OCH₃ |
| Ia.267 | —SCH(CH₃)—CO—OCH₂—CO—OC₂H₅ |
| Ia.268 | —SCH(CH₃)—CO—OCH₂—CO—OCH₂—C₂H₅ |
| Ia.269 | —SCH(CH₃)—CO—OCH₂—CO—OCH(CH₃)₂ |
| Ia.270 | —SCH(CH₃)—CO—OCH₂—CO—OCH₂—CH₂—C₂H₅ |
| Ia.271 | —SCH(CH₃)—CO—OCH₂—CO—OCH₂—CH(CH₃)₂ |
| Ia.272 | —SCH(CH₃)—CO—OCH₂—CO—OCH(CH₃)—C₂H₅ |
| Ia.273 | —SCH(CH₃)—CO—OCH₂—CO—OC(CH₃)₃ |
| Ia.274 | —SCH(CH₃)—CO—OCH(CH₃)—CO—OH |
| Ia.275 | —SCH(CH₃)—CO—OCH(CH₃)—CO—OCH₃ |
| Ia.276 | —SCH(CH₃)—CO—OCH(CH₃)—CO—OC₂H₅ |
| Ia.277 | —SCH(CH₃)—CO—OCH(CH₃)—CO—OCH₂—C₂H₅ |
| Ia.278 | —SCH(CH₃)—CO—OCH(CH₃)—CO—OCH(CH₃)₂ |

TABLE 1-continued

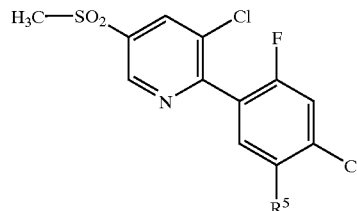

Ia

| No. | $R^5$ |
|---|---|
| Ia.279 | —SCH(CH$_3$)—CO—OCH(CH$_3$)—CO—OCH$_2$—CH$_2$—C$_2$H$_5$ |
| Ia.280 | —SCH(CH$_3$)—CO—OCH(CH$_3$)—CO—OCH$_2$—CH(CH$_3$)$_2$ |
| Ia.281 | —SCH(CH$_3$)—CO—OCH(CH$_3$)—CO—OCH(CH$_3$)—C$_2$H$_5$ |
| Ia.282 | —SCH(CH$_3$)—CO—OCH(CH$_3$)—CO—OC(CH$_3$)$_3$ |
| Ia.283 | —OCH$_2$—CO—NH$_2$ |
| Ia.284 | —OCH$_2$—CO—NH—CH$_3$ |
| Ia.285 | —OCH$_2$—CO—N(CH$_3$)$_2$ |
| Ia.286 | —OCH$_2$—CO—NH—CH$_2$—CO—OH |
| Ia.287 | —OCH$_2$—CO—NH—CH$_2$—CO—OCH$_3$ |
| Ia.288 | —OCH$_2$—CO—NH—CH$_2$—CO—OC$_2$H$_5$ |
| Ia.289 | —OCH$_2$—CO—NH—CH$_2$—CO—OCH$_2$—C$_2$H$_5$ |
| Ia.290 | —OCH$_2$—CO—NH—CH$_2$—CO—OCH$_2$—CH$_2$—C$_2$H$_5$ |
| Ia.291 | —OCH$_2$—CO—NH—CH(CH$_3$)—CO—OH |
| Ia.292 | —OCH$_2$—CO—NH—CH(CH$_3$)—CO—OCH$_3$ |
| Ia.293 | —OCH$_2$—CO—NH—CH(CH$_3$)—CO—OC$_2$H$_5$ |
| Ia.294 | —OCH$_2$—CO—NH—CH(CH$_3$)—CO—OCH$_2$—C$_2$H$_5$ |
| Ia.295 | —OCH$_2$—CO—NH—CH(CH$_3$)—CO—OCH$_2$—CH$_2$—C$_2$H$_5$ |
| Ia.296 | —OCH$_2$—CO—N(CH$_3$)—CH$_2$—CO—OH |
| Ia.297 | —OCH$_2$—CO—N(CH$_3$)—CH$_2$—CO—OCH$_3$ |
| Ia.298 | —OCH$_2$—CO—N(CH$_3$)—CH$_2$—CO—OC$_2$H$_5$ |
| Ia.299 | —OCH$_2$—CO—N(CH$_3$)—CH$_2$—CO—OCH$_2$—C$_2$H$_5$ |
| Ia.300 | —OCH$_2$—CO—N(CH$_3$)—CH$_2$—CO—OCH$_2$—CH$_2$—C$_2$H$_5$ |
| Ia.301 | —OCH$_2$—CO—N(CH$_3$)—CH(CH$_3$)—CO—OH |
| Ia.302 | —OCH$_2$—CO—N(CH$_3$)—CH(CH$_3$)—CO—OCH$_3$ |
| Ia.303 | —OCH$_2$—CO—N(CH$_3$)—CH(CH$_3$)—CO—OC$_2$H$_5$ |
| Ia.304 | —OCH$_2$—CO—N(CH$_3$)—CH(CH$_3$)—CO—OCH$_2$—C$_2$H$_5$ |
| Ia.305 | —OCH$_2$—CO—N(CH$_3$)—CH(CH$_3$)—CO—OCH$_2$—CH$_2$—C$_2$H$_5$ |
| Ia.306 | —OCH(CH$_3$)—CO—NH$_2$ |
| Ia.307 | —OCH(CH$_3$)—CO—NH—CH$_3$ |
| Ia.308 | —OCH(CH$_3$)—CO—N(CH$_3$)$_2$ |
| Ia.309 | —OCH(CH$_3$)—CO—NH—CH$_2$—CO—OH |
| Ia.310 | —OCH(CH$_3$)—CO—NH—CH$_2$—CO—OCH$_3$ |
| Ia.311 | —OCH(CH$_3$)—CO—NH—CH$_2$—CO—OC$_2$H$_5$ |
| Ia.312 | —OCH(CH$_3$)—CO—NH—CH$_2$—CO—OCH$_2$—C$_2$H$_5$ |
| Ia.313 | —OCH(CH$_3$)—CO—NH—CH$_2$—CO—OCH$_2$—CH$_2$—C$_2$H$_5$ |
| Ia.314 | —OCH(CH$_3$)—CO—NH—CH(CH$_3$)—CO—OH |
| Ia.315 | —OCH(CH$_3$)—CO—NH—CH(CH$_3$)—CO—OCH$_3$ |
| Ia.316 | —OCH(CH$_3$)—CO—NH—CH(CH$_3$)—CO—OC$_2$H$_5$ |
| Ia.317 | —OCH(CH$_3$)—CO—NH—CH(CH$_3$)—CO—OCH$_2$—C$_2$H$_5$ |
| Ia.318 | —OCH(CH$_3$)—CO—NH—CH(CH$_3$)—CO—OCH$_2$—CH$_2$—C$_2$H$_5$ |
| Ia.319 | —OCH(CH$_3$)—CO—N(CH$_3$)—CH$_2$—CO—OH |
| Ia.320 | —OCH(CH$_3$)—CO—N(CH$_3$)—CH$_2$—CO—OCH$_3$ |
| Ia.321 | —OCH(CH$_3$)—CO—N(CH$_3$)—CH$_2$—CO—OC$_2$H$_5$ |
| Ia.322 | —OCH(CH$_3$)—CO—N(CH$_3$)—CH$_2$—CO—OCH$_2$—C$_2$H$_5$ |
| Ia.323 | —OCH(CH$_3$)—CO—N(CH$_3$)—CH$_2$—CO—OCH$_2$—CH$_2$—C$_2$H$_5$ |
| Ia.324 | —OCH(CH$_3$)—CO—N(CH$_3$)—CH(CH$_3$)—CO—OH |
| Ia.325 | —OCH(CH$_3$)—CO—N(CH$_3$)—CH(CH$_3$)—CO—OCH$_3$ |
| Ia.326 | —OCH(CH$_3$)—CO—N(CH$_3$)—CH(CH$_3$)—CO—OC$_2$H$_5$ |
| Ia.327 | —OCH(CH$_3$)—CO—N(CH$_3$)—CH(CH$_3$)—CO—OCH$_2$—C$_2$H$_5$ |
| Ia.328 | —OCH(CH$_3$)—CO—N(CH$_3$)—CH(CH$_3$)—CO—OCH$_2$—CH$_2$—C$_2$H$_5$ |
| Ia.329 | —SCH$_2$—CO—NH$_2$ |
| Ia.330 | —SCH$_2$—CO—NH—CH$_3$ |
| Ia.331 | —SCH$_2$—CO—N(CH$_3$)$_2$ |
| Ia.332 | —SCH$_2$—CO—NH—CH$_2$—CO—OH |
| Ia.333 | —SCH$_2$—CO—NH—CH$_2$—CO—OCH$_3$ |
| Ia.334 | —SCH$_2$—CO—NH—CH$_2$—CO—OC$_2$H$_5$ |
| Ia.335 | —SCH$_2$—CO—NH—CH$_2$—CO—OCH$_2$—C$_2$H$_5$ |
| Ia.336 | —SCH$_2$—CO—NH—CH$_2$—CO—OCH$_2$—CH$_2$—C$_2$H$_5$ |
| Ia.337 | —SCH$_2$—CO—NH—CH(CH$_3$)—CO—OH |
| Ia.338 | —SCH$_2$—CO—NH—CH(CH$_3$)—CO—OCH$_3$ |
| Ia.339 | —SCH$_2$—CO—NH—CH(CH$_3$)—CO—OC$_2$H$_5$ |
| Ia.340 | —SCH$_2$—CO—NH—CH(CH$_3$)—CO—OCH$_2$—C$_2$H$_5$ |
| Ia.341 | —SCH$_2$—CO—NH—CH(CH$_3$)—CO—OCH$_2$—CH$_2$—C$_2$H$_5$ |
| Ia.342 | —SCH$_2$—CO—N(CH$_3$)—CH$_2$—CO—OH |

TABLE 1-continued

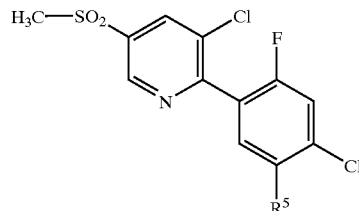

Ia

| No. | R⁵ |
|---|---|
| Ia.343 | —SCH₂—CO—N(CH₃)—CH₂—CO—OCH₃ |
| Ia.344 | —SCH₂—CO—N(CH₃)—CH₂—CO—OC₂H₅ |
| Ia.345 | —SCH₂—CO—N(CH₃)—CH₂—CO—OCH₂—C₂H₅ |
| Ia.346 | —SCH₂—CO—N(CH₃)—CH₂—CO—OCH₂—CH₂—C₂H₅ |
| Ia.347 | —SCH₂—CO—N(CH₃)—CH(CH₃)—CO—OH |
| Ia.348 | —SCH₂—CO—N(CH₃)—CH(CH₃)—CO—OCH₃ |
| Ia.349 | —SCH₂—CO—N(CH₃)—CH(CH₃)—CO—OC₂H₅ |
| Ia.350 | —SCH₂—CO—N(CH₃)—CH(CH₃)—CO—OCH₂—C₂H₅ |
| Ia.351 | —SCH₂—CO—N(CH₃)—CH(CH₃)—CO—OCH₂—CH₂—C₂H₅ |
| Ia.352 | —SCH(CH₃)—CO—NH₂ |
| Ia.353 | —SCH(CH₃)—CO—NH—CH₃ |
| Ia.354 | —SCH(CH₃)—CO—N(CH₃)₂ |
| Ia.355 | —SCH(CH₃)—CO—NH—CH₂—CO—OH |
| Ia.356 | —SCH(CH₃)—CO—NH—CH₂—CO—OCH₃ |
| Ia.357 | —SCH(CH₃)—CO—NH—CH₂—CO—OC₂H₅ |
| Ia.358 | —SCH(CH₃)—CO—NH—CH₂—CO—OCH₂—C₂H₅ |
| Ia.359 | —SCH(CH₃)—CO—NH—CH₂—CO—OCH₂—CH₂—C₂H₅ |
| Ia.360 | —SCH(CH₃)—CO—NH—CH(CH₃)—CO—OH |
| Ia.361 | —SCH(CH₃)—CO—NH—CH(CH₃)—CO—OCH₃ |
| Ia.362 | —SCH(CH₃)—CO—NH—CH(CH₃)—CO—OC₂H₅ |
| Ia.363 | —SCH(CH₃)—CO—NH—CH(CH₃)—CO—OCH₂—C₂H₅ |
| Ia.364 | —SCH(CH₃)—CO—NH—CH(CH₃)—CO—OCH₂—CH₂—C₂H₅ |
| Ia.365 | —SCH(CH₃)—CO—N(CH₃)—CH₂—CO—OH |
| Ia.366 | —SCH(CH₃)—CO—N(CH₃)—CH₂—CO—OCH₃ |
| Ia.367 | —SCH(CH₃)—CO—N(CH₃)—CH₂—CO—OC₂H₅ |
| Ia.368 | —SCH(CH₃)—CO—N(CH₃)—CH₂—CO—OCH₂—C₂H₅ |
| Ia.369 | —SCH(CH₃)—CO—N(CH₃)—CH₂—CO—OCH₂—CH₂—C₂H₅ |
| Ia.370 | —SCH(CH₃)—CO—N(CH₃)—CH(CH₃)—CO—OH |
| Ia.371 | —SCH(CH₃)—CO—N(CH₃)—CH(CH₃)—CO—OCH₃ |
| Ia.372 | —SCH(CH₃)—CO—N(CH₃)—CH(CH₃)—CO—OC₂H₅ |
| Ia.373 | —SCH(CH₃)—CO—N(CH₃)—CH(CH₃)—CO—OCH₂—C₂H₅ |
| Ia.374 | —SCH(CH₃)—CO—N(CH₃)—CH(CH₃)—CO—OCH₂—CH₂—C₂H₅ |
| Ia.375 | —OCH₂—CO-[2-(COOCH₃)-pyrrolidin-1-yl] |
| Ia.376 | —OCH₂—CO-[2-(COOC₂H₅)-pyrrolidin-1-yl] |
| Ia.377 | —OCH(CH₃)—CO-[2-(COOCH₃)-pyrrolidin-1-yl] |
| Ia.378 | —OCH(CH₃)—CO-[2-(COOC₂H₅)-pyrrolidin-1-yl] |
| Ia.379 | —SCH₂—CO-[2-(COOCH₃)-pyrrolidin-1-yl] |
| Ia.380 | —SCH₂—CO-[2-(COOC₂H₅)-pyrrolidin-1-yl] |
| Ia.381 | —SCH(CH₃)—CO-[2-(COOCH₃)-pyrrolidin-1-yl] |
| Ia.382 | —SCH(CH₃)—CO-[2-(COOC₂H₅)-pyrrolidin-1-yl] |
| Ia.383 | —OH |
| Ia.384 | —OCH₃ |
| Ia.385 | —OC₂H₅ |
| Ia.386 | —OCH₂—C₂H₅ |
| Ia.387 | —OCH(CH₃)₂ |
| Ia.388 | —OCH₂—CH₂—C₂H₅ |
| Ia.389 | —OCH(CH₃)—C₂H₅ |
| Ia.390 | —OCH₂—CH(CH₃)₂ |
| Ia.391 | —OCH₂—CH₂—CH₂—C₂H₅ |
| Ia.392 | —OCH₂—CH₂—CH(CH₃)—CH₃ |
| Ia.393 | —OCH₂—CF₃ |
| Ia.394 | —OCHF₂ |
| Ia.395 | —OCH₂—CH=CH₂ |
| Ia.396 | —OCH₂—CH=CH—CH₃ |
| Ia.397 | —OCH₂—CH(CH₃)=CH₂ |
| Ia.398 | —OCH(CH₃)—CH=CH₂ |
| Ia.399 | —OCH₂—CH=CH—C₂H₅ |
| Ia.400 | —OCH₂—CH₂—CH=CH—CH₃ |
| Ia.401 | —OCH₂—CH₂—CH₂—CH=CH₂ |
| Ia.402 | —OCH₂—C≡CH |
| Ia.403 | —OCH(CH₃)—C≡CH |
| Ia.404 | —OCH₂—C≡C—CH₃ |
| Ia.405 | —OCH₂—C≡C—C₂H₅ |
| Ia.406 | cyclopropyloxy |

TABLE 1-continued

[Structure Ia: A pyridine ring with H₃C—SO₂ group and Cl substituent, connected to a phenyl ring bearing F, Cl, and R⁵ substituents]

| No. | R⁵ |
|---|---|
| Ia.407 | cyclobutyloxy |
| Ia.408 | cyclopentyloxy |
| Ia.409 | cyclohexyloxy |
| Ia.410 | —OCH₂—CH₂—OCH₃ |
| Ia.411 | —OCH₂—CH₂—OC₂H₅ |
| Ia.412 | —OCH₂—CH₂—OCH₂—C₂H₅ |
| Ia.413 | —OCH₂—CH₂—OCH(CH₃)₂ |
| Ia.414 | —SH |
| Ia.415 | —SCH₃ |
| Ia.416 | —SC₂H₅ |
| Ia.417 | —SCH₂—C₂H₅ |
| Ia.418 | —SCH(CH₃)₂ |
| Ia.419 | —SCH₂—CH₂—C₂H₅ |
| Ia.420 | —SCH(CH₃)—C₂H₅ |
| Ia.421 | —SCH₂—CH(CH₃)₂ |
| Ia.422 | —SCH₂—CH₂—CH₂—C₂H₅ |
| Ia.423 | —SCH₂—CH₂—CH(CH₃)—CH₃ |
| Ia.424 | —SCH₂—CF₃ |
| Ia.425 | —SCHF₂ |
| Ia.426 | —SCH₂—CH=CH₂ |
| Ia.427 | —SCH₂—CH=CH—CH₃ |
| Ia.428 | —SCH₂—CH(CH₃)=CH₂ |
| Ia.429 | —SCH(CH₃)—CH=CH₂ |
| Ia.430 | —SCH₂—CH=CH—C₂H₅ |
| Ia.431 | —SCH₂—CH₂—CH=CH—CH₃ |
| Ia.432 | —SCH₂—CH₂—CH₂—CH=CH₂ |
| Ia.433 | —SCH₂—C≡CH |
| Ia.434 | —SCH(CH₃)—C≡CH |
| Ia.435 | —SCH₂—C≡C—CH₃ |
| Ia.436 | —SCH₂—C≡C—C₂H₅ |
| Ia.437 | cyclopropylthio |
| Ia.438 | cyclobutylthio |
| Ia.439 | cyclopentylthio |
| Ia.440 | cyclohexylthio |
| Ia.441 | —SCH₂—CH₂—OCH₃ |
| Ia.442 | —SCH₂—CH₂—OC₂H₅ |
| Ia.443 | —SCH₂—CH₂—OCH₂—C₂H₅ |
| Ia.444 | —SCH₂—CH₂—OCH(CH₃)₂ |
| Ia.445 | —CH=CH₂—CO—OH |
| Ia.446 | —CH=CH₂—CO—OCH₃ |
| Ia.447 | —CH=CH₂—CO—OC₂H₅ |
| Ia.448 | —CH=CH₂—CO—OCH₂—C₂H₅ |
| Ia.449 | —CH=CH₂—CO—OCH₂—CH₂—C₂H₅ |
| Ia.450 | —CH=CH(Cl)—CO—OH |
| Ia.451 | —CH=CH(Cl)—CO—OCH₃ |
| Ia.452 | —CH=CH(Cl)—CO—OC₂H₅ |
| Ia.453 | —CH=CH(Cl)—CO—OCH₂—C₂H₅ |
| Ia.454 | —CH=CH(Cl)—CO—OCH₂—CH₂—C₂H₅ |
| Ia.455 | —CH=CH(CH₃)—CO—OH |
| Ia.456 | —CH=CH(CH₃)—CO—OCH₃ |
| Ia.457 | —CH=CH(CH₃)—CO—OC₂H₅ |
| Ia.458 | —CH=CH(CH₃)—CO—OCH₂—C₂H₅ |
| Ia.459 | —CH=CH(CH₃)—CO—OCH₂—CH₂—C₂H₅ |
| Ia.460 | —CH=CH—CO—NH₂ |
| Ia.461 | —CH=CH—CO—NH—CH₃ |
| Ia.462 | —CH=CH—CO—N(CH₃)₂ |
| Ia.463 | —CH=CH—CO—NH—CH₂—CO—OH |
| Ia.464 | —CH=CH—CO—NH—CH₂—CO—OCH₃ |
| Ia.465 | —CH=CH—CO—NH—CH₂—CO—OC₂H₅ |
| Ia.466 | —CH=CH—CO—NH—CH(CH₃)—CO—OH |
| Ia.467 | —CH=CH—CO—NH—CH(CH₃)—CO—OCH₃ |
| Ia.468 | —CH=CH—CO—NH—CH(CH₃)—CO—OC₂H₅ |
| Ia.469 | —CH=CH—CO—N(CH₃)—CH₂—CO—OH |
| Ia.470 | —CH=CH—CO—N(CH₃)—CH₂—CO—OCH₃ |

TABLE 1-continued

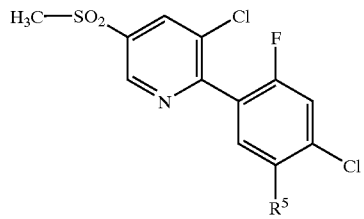

| No. | R⁵ |
|---|---|
| Ia.471 | —CH=CH—CO—N(CH₃)—CH₂—CO—OC₂H₅ |
| Ia.472 | —CH=CH—CO—N(CH₃)—CH(CH₃)—CO—OH |
| Ia.473 | —CH=CH—CO—N(CH₃)—CH(CH₃)—CO—OCH₃ |
| Ia.474 | —CH=CH—CO—N(CH₃)—CH(CH₃)—CO—OC₂H₅ |
| Ia.475 | —CH=C(Cl)—CO—NH—CH(CH₃)—CO—OH |
| Ia.476 | —CH=C(Cl)—CO—NH—CH(CH₃)—CO—OCH₃ |
| Ia.477 | —CH=C(Cl)—CO—NH—CH(CH₃)—CO—OC₂H₅ |
| Ia.478 | —CH=C(Cl)—CO—N(CH₃)—CH₂—CO—OH |
| Ia.479 | —CH=C(Cl)—CO—N(CH₃)—CH₂—CO—OCH₃ |
| Ia.480 | —CH=C(Cl)—CO—N(CH₃)—CH₂—CO—OC₂H₅ |
| Ia.481 | —CH=C(Cl)—CO—N(CH₃)—CH(CH₃)—CO—OH |
| Ia.482 | —CH=C(Cl)—CO—N(CH₃)—CH(CH₃)—CO—OCH₃ |
| Ia.483 | —CH=C(Cl)—CO—N(CH₃)—CH(CH₃)—CO—OC₂H₅ |
| Ia.484 | —CH=C(Cl)—CO-[2-(COOCH₃)-pyrrolidin-1-yl] |
| Ia.485 | —CH=C(Cl)—CO-[2-(COOC₂H₅)-pyrrolidin-1-yl] |
| Ia.486 | —CHO |
| Ia.487 | —CO—CH₃ |
| Ia.488 | —CO—C₂H₅ |
| Ia.489 | —CO—CH₂—C₂H₅ |
| Ia.490 | —CO—CH(CH₃)₂ |
| Ia.491 | —CO—CH₂—CH₂—C₂H₅ |
| Ia.492 | —CO—CH₂—CH(CH₃)—CH₃ |
| Ia.493 | —CO—CH(CH₃)—C₂H₅ |
| Ia.494 | —CO—CH₂—Cl |
| Ia.495 | —CO—CH₂—Br |
| Ia.496 | —CO—CHCl₂ |
| Ia.497 | —CO—CHBr₂ |
| Ia.498 | —CO—CCl₃ |
| Ia.499 | —CO—CF₃ |
| Ia.500 | —CH=CH—CO-[2-(COOCH₃)-pyrrolidin-1-yl] |
| Ia.501 | —CH=CH—CO-[2-(COOC₂H₅)-pyrrolidin-1-yl] |
| Ia.502 | —CH=C(CH₃)—CO—NH₂ |
| Ia.503 | —CH=C(CH₃)—CO—NH—CH₃ |
| Ia.504 | —CH=C(CH₃)—CO—N(CH₃)₂ |
| Ia.505 | —CH=C(CH₃)—CO—NH—CH₂—CO—OH |
| Ia.506 | —CH=C(CH₃)—CO—NH—CH₂—CO—OCH₃ |
| Ia.507 | —CH=C(CH₃)—CO—NH—CH₂—CO—OC₂H₅ |
| Ia.508 | —CH=C(CH₃)—CO—NH—CH(CH₃)—CO—OH |
| Ia.509 | —CH=C(CH₃)—CO—NH—CH(CH₃)—CO—OCH₃ |
| Ia.510 | —CH=C(CH₃)—CO—NH—CH(CH₃)—CO—OC₂H₅ |
| Ia.511 | —CH=C(CH₃)—CO—N(CH₃)—CH₂—CO—OH |
| Ia.512 | —CH=C(CH₃)—CO—N(CH₃)—CH₂—CO—OCH₃ |
| Ia.513 | —CH=C(CH₃)—CO—N(CH₃)—CH₂—CO—OC₂H₅ |
| Ia.514 | —CH=C(CH₃)—CO—N(CH₃)—CH(CH₃)—CO—OH |
| Ia.515 | —CH=C(CH₃)—CO—N(CH₃)—CH(CH₃)—CO—OCH₃ |
| Ia.516 | —CH=C(CH₃)—CO—N(CH₃)—CH(CH₃)—CO—OC₂H₅ |
| Ia.517 | —CH=C(CH₃)—CO-[2-(COOCH₃)-pyrrolidin-1-yl] |
| Ia.518 | —CH=C(CH₃)—CO-[2-(COOC₂H₅)-pyrrolidin-1-yl] |
| Ia.519 | —CH=C(Cl)—CO—NH₂ |
| Ia.520 | —CH=C(Cl)—CO—NH—CH₃ |
| Ia.521 | —CH=C(Cl)—CO—N(CH₃)₂ |
| Ia.522 | —CH=C(Cl)—CO—NH—CH₂—CO—OH |
| Ia.523 | —CH=C(Cl)—CO—NH—CH₂—CO—OCH₃ |
| Ia.524 | —CH=C(Cl)—CO—NH—CH₂—CO—OC₂H₅ |
| Ia.525 | —CO—CH₂—CH=CH₂ |
| Ia.526 | —CO—CH₂—CH=CH—CH₃ |
| Ia.527 | —CO—CH₂—CH₂—CH=CH₂ |
| Ia.528 | —CO—CH₂—C≡CH |
| Ia.529 | —CO—CH(CH₃)—C≡CH |
| Ia.530 | —CO—CH₂—C≡C—CH₃ |
| Ia.531 | cyclopropylcarbonyl |
| Ia.532 | cyclobutylcarbonyl |
| Ia.533 | cyclopentylcarbonyl |
| Ia.534 | cyclohexylcarbonyl |

TABLE 1-continued

[Structure: pyridine with H₃C—SO₂ at position 5, Cl at position 3, connected at position 2 to a phenyl ring bearing F (ortho), Cl (para to F), and R⁵]

Ia

| No. | R⁵ |
|---|---|
| Ia.535 | —CO—CH₂—OCH₃ |
| Ia.536 | —CO—CH₂—OC₂H₅ |
| Ia.537 | —CO—CH₂—CH₂—OCH₃ |
| Ia.538 | —CO—CH₂—CH₂—OC₂H₅ |
| Ia.539 | 1,3-dioxolan-2-yl |
| Ia.540 | 4-(CH₃)-1,3-dioxolan-2-yl |
| Ia.541 | 4,5-(CH₃)₂-1,3-dioxolan-2-yl |
| Ia.542 | 4,4-(CH₃)₂-1,3-dioxolan-2-yl |
| Ia.543 | 4,4,5-(CH₃)₃-1,3-dioxolan-2-yl |
| Ia.544 | 4,4,5,5-(CH₃)₄-1,3-dioxolan-2-yl |
| Ia.545 | 4-(COOCH₃)-1,3-dioxolan-2-yl |
| Ia.546 | 4-(COOC₂H₅)-1,3-dioxolan-2-yl |
| Ia.547 | 4-(COOCH₂C₂H₅)-1,3-dioxolan-2-yl |
| Ia.548 | 4-[COOCH(CH₃)₂]-1,3-dioxolan-2-yl |
| Ia.549 | 4-(COOCH₂CH₂—C₂H₅)-1,3-dioxolan-2-yl |
| Ia.550 | 4-[COOCH₂CH(CH₃)₂]-1,3-dioxolan-2-yl |
| Ia.551 | 4-[COOCH(CH₃)C₂H₅]-1,3-dioxolan-2-yl |
| Ia.552 | 4-[COOC(CH₃)₃]-1,3-dioxolan-2-yl |
| Ia.553 | 4,5-(COOCH₃)₂-1,3-dioxolan-2-yl |
| Ia.554 | 4,5-(COOC₂H₅)₂-1,3-dioxolan-2-yl |
| Ia.555 | [1,3-oxathiolan-2-yl structure] |
| Ia.556 | 1,3-Dithiolan-2-yl |
| Ia.557 | 4-(CH₃)-1,3-dithiolan-2-yl |
| Ia.558 | 4,5-(CH₃)₂-1,3-dithiolan-2-yl |
| Ia.559 | 4,4-(CH₃)₂-1,3-dithiolan-2-yl |
| Ia.560 | 4-(COOCH₃)-1,3-dithiolan-2-yl |
| Ia.561 | 4-(COOC₂H₅)-1,3-dithiolan-2-yl |
| Ia.562 | 4-(COOCH₂C₂H₅)-1,3-dithiolan-2-yl |
| Ia.563 | 4-[COOCH(CH₃)₂]-1,3-dithiolan-2-yl |
| Ia.564 | 4-(COOCH₂CH₂C₂H₅)-1,3-dithiolan-2-yl |
| Ia.565 | 4-[COOCH₂CH(CH₃)₂]-1,3-dithiolan-2-yl |
| Ia.566 | 4-[COOCH(CH₃)C₂H₅]-1,3-dithiolan-2-yl |
| Ia.567 | 4-[COOC(CH₃)₃]-1,3-dithiolan-2-yl |
| Ia.568 | 4,5-(COOCH₃)₂-1,3-dithiolan-2-yl |
| Ia.569 | 4,5-(COOC₂H₅)₂-1,3-dithiolan-2-yl |
| Ia.570 | —CH=N—OH |
| Ia.571 | —CH=N—OCH₃ |
| Ia.572 | —CH=N—OC₂H₅ |
| Ia.573 | —CH=N—OCH₂—C₂H₅ |
| Ia.574 | —CH=N—OCH(CH₃)₂ |
| Ia.575 | —CH=N—OCH₂—CH₂—C₂H₅ |
| Ia.576 | —CH=N—OCH₂—CH(CH₃)₂ |
| Ia.577 | —CH=N—OCH(CH₃)—C₂H₅ |
| Ia.578 | —CH=N—OC(CH₃)₃ |
| Ia.579 | —CH=N—OCH₂—CH₂—CH₂—C₂H₅ |
| Ia.580 | —CH=N—OCH₂—CH₂—CH(CH₃)₂ |
| Ia.581 | —CH=N—OCH₂—CO—OCH₃ |
| Ia.582 | —CH=N—OCH₂—CO—OC₂H₅ |
| Ia.583 | —CH=N—OCH₂—CO—OCH₂—C₂H₅ |
| Ia.584 | —CH=N—OCH(CH₃)—CO—OCH₃ |
| Ia.585 | —CH=N—OCH(CH₃)—CO—OC₂H₅ |
| Ia.586 | —CH=N—OCH(CH₃)—CO—OCH₂—C₂H₅ |
| Ia.587 | —CH(OCH₃)₂ |
| Ia.588 | —CH(OC₂H₅)₂ |
| Ia.589 | —CH(OCH₂—C₂H₅)₂ |
| Ia.590 | —CH(OCH₂—CH₂—C₂H₅)₂ |
| Ia.591 | —NO₂ |
| Ia.592 | —NH—OH |
| Ia.593 | —NH₂ |

TABLE 1-continued

Ia

Structure: 5-(methylsulfonyl)-3-chloro-2-(2-fluoro-4-chloro-5-R⁵-phenyl)pyridine

| No. | R⁵ |
|---|---|
| Ia.594 | —NH—CH$_3$ |
| Ia.595 | —N(CH$_3$)$_2$ |
| Ia.596 | —NH—CH$_2$—CO—OCH$_3$ |
| Ia.597 | —NH—CH$_2$—CO—OC$_2$H$_5$ |
| Ia.598 | —NH—CH$_2$—CO—OCH$_2$—C$_2$H$_5$ |
| Ia.599 | —NH—CH$_2$—CO—OCH$_2$—CH$_2$—C$_2$H$_5$ |
| Ia.600 | —NH—CH(CH$_3$)—CO—OCH$_3$ |
| Ia.601 | —NH—CH(CH$_3$)—CO—OC$_2$H$_5$ |
| Ia.602 | —NH—CH(CH$_3$)—CO—OCH$_2$—C$_2$H$_5$ |
| Ia.603 | —NH—CH(CH$_3$)—CO—OCH$_2$—CH$_2$—C$_2$H$_5$ |
| Ia.604 | —N(CH$_3$)—CH$_2$—CO—OCH$_3$ |
| Ia.605 | —N(CH$_3$)—CH$_2$—CO—OC$_2$H$_5$ |
| Ia.606 | —N(CH$_3$)—CH$_2$—CO—OCH$_2$—C$_2$H$_5$ |
| Ia.607 | —N(CH$_3$)—CH$_2$—CO—OCH$_2$—CH$_2$—C$_2$H$_5$ |
| Ia.608 | —N(CH$_3$)—CH(CH$_3$)—CO—OCH$_3$ |
| Ia.609 | —N(CH$_3$)—CH(CH$_3$)—CO—OC$_2$H$_5$ |
| Ia.610 | —N(CH$_3$)—CH(CH$_3$)—CO—OCH$_2$—C$_2$H$_5$ |
| Ia.611 | —N(CH$_3$)—CH(CH$_3$)—CO—OCH$_2$—CH$_2$—C$_2$H$_5$ |
| Ia.612 | —NH—SO$_2$—CH$_3$ |
| Ia.613 | —NH—SO$_2$—C$_2$H$_5$ |
| Ia.614 | —NH—SO$_2$—CH$_2$—C$_2$H$_5$ |
| Ia.615 | —NH—SO$_2$—CH(CH$_3$)$_2$ |
| Ia.616 | —NH—SO$_2$—CH$_2$—CH$_2$—C$_2$H$_5$ |
| Ia.617 | —NH—SO$_2$—CH$_2$—CH(CH$_3$)$_2$ |
| Ia.618 | —NH—SO$_2$—CH(CH$_3$)—C$_2$H$_5$ |
| Ia.619 | —N(CH$_3$)—SO$_2$—CH$_3$ |
| Ia.620 | —N(CH$_3$)—SO$_2$—C$_2$H$_5$ |
| Ia.621 | —N(CH$_3$)—SO$_2$—CH$_2$—C$_2$H$_5$ |
| Ia.622 | —N(CH$_3$)—SO$_2$—CH(CH$_3$)$_2$ |
| Ia.623 | —N(CH$_3$)—SO$_2$—CH$_2$—CH$_2$—C$_2$H$_5$ |
| Ia.624 | —N(CH$_3$)—SO$_2$—CH$_2$—CH(CH$_3$)$_2$ |
| Ia.625 | —NH—CO—CH$_3$ |
| Ia.626 | —NH—CO—C$_2$H$_5$ |
| Ia.627 | —NH—CO—CH$_2$—C$_2$H$_5$ |
| Ia.628 | —NH—CO—CH(CH$_3$)$_2$ |
| Ia.629 | —NH—CO—CH$_2$—CH$_2$—C$_2$H$_5$ |
| Ia.630 | —NH—CO—CH$_2$—CH(CH$_3$)$_2$ |
| Ia.631 | —NH—CO—CH(CH$_3$)—C$_2$H$_5$ |
| Ia.632 | —NH—CO—C(CH$_3$)$_3$ |
| Ia.633 | —N(CH$_3$)—CO—CH$_3$ |
| Ia.634 | —N(CH$_3$)—CO—C$_2$H$_5$ |
| Ia.635 | —N(CH$_3$)—CO—CH$_2$—C$_2$H$_5$ |
| Ia.636 | —N(CH$_3$)—CO—CH(CH$_3$)$_2$ |
| Ia.637 | —N(CH$_3$)—CO—CH$_2$—CH$_2$—C$_2$H$_5$ |
| Ia.638 | —N(CH$_3$)—CO—CH$_2$—CH(CH$_3$)$_2$ |
| Ia.639 | —N(CH$_3$)—CO—CH(CH$_3$)—C$_2$H$_5$ |
| Ia.640 | —N(CH$_3$)—CO—C(CH$_3$)$_3$ |
| Ia.641 | —SO$_2$—Cl |
| Ia.642 | —SO$_2$—OH |
| Ia.643 | —SO$_2$—NH$_2$ |
| Ia.644 | —SO$_2$—NH—CH$_3$ |
| Ia.645 | —SO$_2$—N(CH$_3$)$_2$ |
| Ia.646 | —SO$_2$—NH—CH$_2$—CO—OCH$_3$ |
| Ia.647 | —SO$_2$—NH—CH$_2$—CO—OC$_2$H$_5$ |
| Ia.648 | —SO$_2$—NH—CH(CH$_3$)—CO—OCH$_3$ |
| Ia.649 | —SO$_2$—NH—CH(CH$_3$)—CO—OC$_2$H$_5$ |
| Ia.650 | —SO$_2$—N(CH$_3$)—CH$_2$—CO—OCH$_3$ |
| Ia.651 | —SO$_2$—N(CH$_3$)—CH$_2$—CO—OC$_2$H$_5$ |
| Ia.652 | —SO$_2$—N(CH$_3$)—CH(CH$_3$)—CO—OCH$_3$ |
| Ia.653 | —SO$_2$—N(CH$_3$)—CH(CH$_3$)—CO—OC$_2$H$_5$ |
| Ia.654 | 1,3-dioxan-2-yl |
| Ia.655 | 4-(CH$_3$)-1,3-dioxan-2-yl |
| Ia.656 | 5-(CH$_3$)-1,3-dioxan-2-yl |
| Ia.657 | 5,5-(CH$_3$)$_2$-1,3-dioxan-2-yl |

TABLE 1-continued

Ia

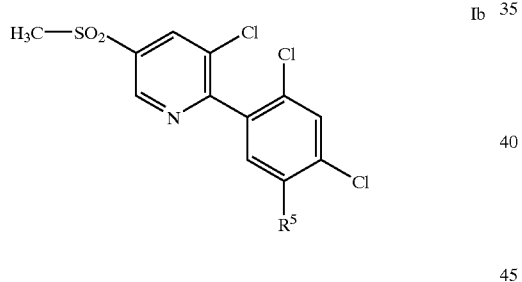

| No. | R⁵ |
|---|---|
| Ia.658 | (structure shown) |
| Ia.659 | 1,3-dithian-2-yl |
| Ia.660 | 4-(CH₃)-dithian-2-yl |
| Ia.661 | 5-(CH₃)-dithian-2-yl |
| Ia.662 | 5,5-(CH₃)₂-dithian-2-yl |

Other very especially preferred substituted 2-phenylpyridines are those of the formulae Ib, Ic, Id, Ie and If, in particular the compounds Ib.1 to Ib.662, which differ from the corresponding compounds Ia.1 to Ia.662 only in that $R^3$ is chlorine:

Ib

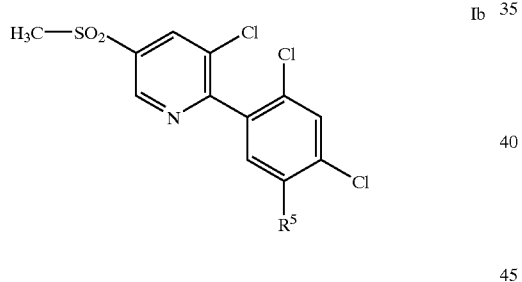

the compounds Ic.1 to Ic.662, which differ from the corresponding compounds Ia.1 to Ia.662 only in that $R^3$ is hydrogen:

Ic

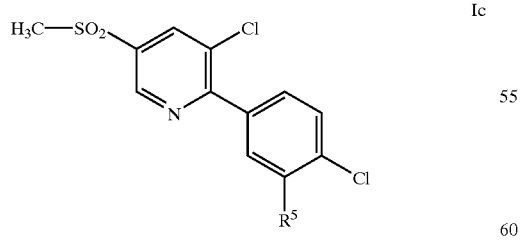

the compounds Id.1 to Id.662, which differ from the corresponding compounds Ia.1 to Ia.662 only in that $R^3$ is cyano:

Id

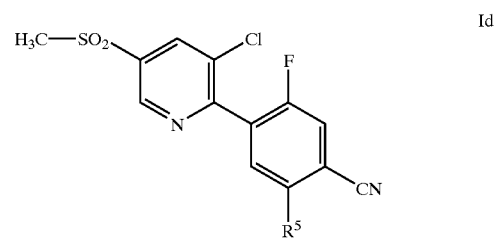

the compounds Ie.1 to Ie.662, which differ from the corresponding compounds Ia.1 to Ia.662 only in that $R^3$ is chlorine and $R^4$ is cyano:

Ie

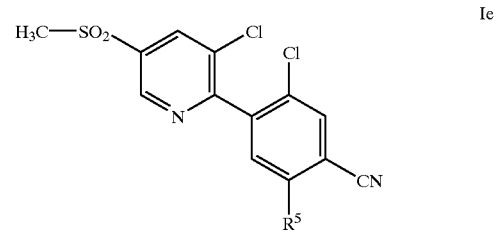

the compounds If.1 to If.662, which differ from the corresponding compounds Ia.1 to Ia.662 only in that $R^3$ is hydrogen and $R^4$ is cyano:

If

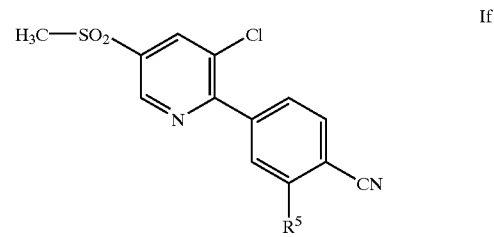

The substituted 2-phenylpyridines of the formula I are accessible in various ways, for example by one of the following processes:

Process A

Oxidation of substituted 2-phenylpyridines of the formula I where n is zero and $R^1$ and $R^5$ do not contain oxidizable sulfur, in a manner known per se {cf. for example, A. Albini & S. Pietra, Heterocyclic N-Oxides, CRC-Press Inc., Boca Raton, USA 1991; H. S. Mosher et al., Org. Synth. Coll. Vol. IV 1963, page 828; E. C. Taylor et al., Org. Synth. Coll. Vol. IV 1963, page 704; T. W. Bell et. al., Org. Synth. 69 (1990), page 226}:

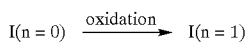

Among the oxidants conventionally used for oxidizing the pyridine ring, reference may be made by way of example to peracetic acid, trifluoroperacetic acid, perbenzoic acid, m-chloroperbenzoic acid, monopermaleic acid, magnesium monoperphthalate, sodium perborate, Oxone® (contains peroxydisulfate), pertungstic acid and hydrogen peroxide.

Examples of suitable solvents are water, sulfuric acid, carboxylic acids such as acetic acid and trifluoroacetic acid, and also halogenated hydrocarbons such as dichloromethane and chloroform.

The oxidation is normally successfully carried out at from 0° C. to the boiling point of the reaction mixture.

The oxidant is normally employed in at least equimolar amounts based on the starting compound. In general, an excess of oxidant has proved to be especially advantageous.

Process B

Oxidation of substituted 2-phenylpyridines of the formula I where $R^1$ is $C_1$–$C_6$-alkylthio or $C_1$–$C_6$-alkylsulfinyl and the substituent $R^5$ does not contain oxidizable sulfur, in a manner known per se {cf., for example, C. S. Giam et al., Org. Prep. Proced. Int. 13(2) (1981), p. 137; S. G. Woods et al., J. Heterocycl. Chem. 21 (1984), 97–101; S. G. Woods, U.S. Pat. No. 4,616,087; N. Finch et al., J. Med. Chem. 21(12) (1978), 1269–1274; H. Ban-Oganowska, Pd. J. Chem. 67(9) (1993), 1609–1613; A. D. Dunn & R. Norrie, J. Prakt. Chem./Chem.-Ztg. 335 (1993), 269–272}:

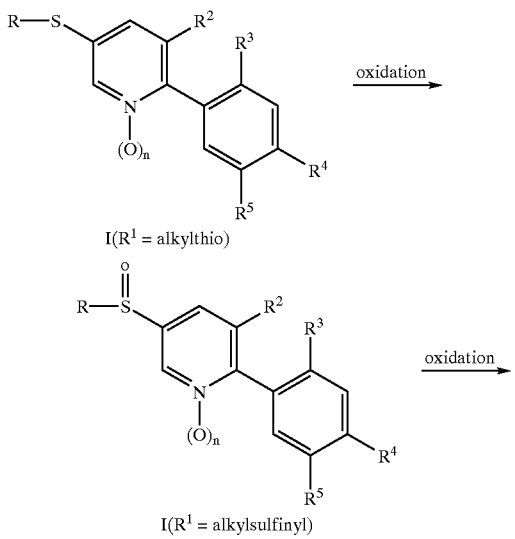

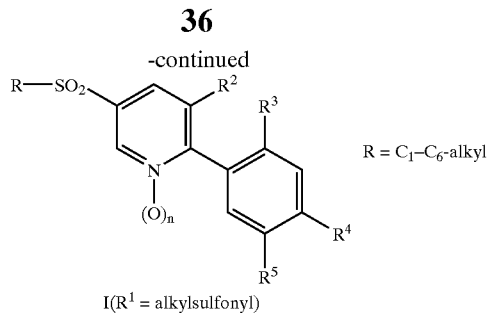

As regards suitable solvents and reaction temperatures, reference may be made to the information given for Process A). Oxidants which are suitable in addition to those mentioned for Process A) are also alkali metal hypohalites such as sodium hypochlorite and potassium hypochlorite.

To prepare products of value I where $R^1$=alkylsulfinyl, it is recommended to employ not more than approx. 1.1 equivalents of the oxidant. To prepare I where $R^1$=alkylsulfonyl, it is necessary to employ at least one equivalent or at least two equivalents of the oxidant, depending on whether the starting material is a corresponding compound I where $R^1$=alkylthio or a corresponding compound I where $R^1$=alkylsulfinyl.

Process C

Transition-metal-catalyzed cross-coupling reaction of 2-halopyridines II (Hal=chlorine or bromine) with organometallic compounds of the formula III in a manner known per se {cf., for example, WO 95/02580 and the literature cited therein on pages 21 and 22}:

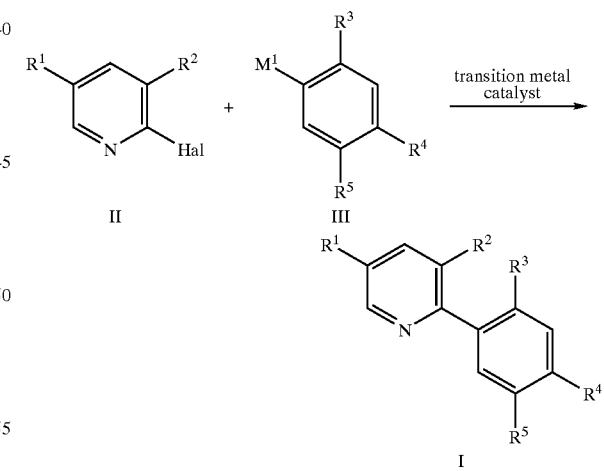

$M^1$ is $B(OH)_2$, Mg—Cl, Mg—Br, Mg—I, Zn—Cl, Zn—Br, Zn—I, lithium, copper or tin-tri($C_1$–$C_4$-alkyl), preferably $B(OH)_2$, Mg—Cl, Mg—Br, Mg—I, Zn—Cl, Zn—Br or Zn—I.

Alternatively, it is also possible to employ the boron oxines IV instead of the boronic acids III {$M^1$=$B(OH)_2$}.

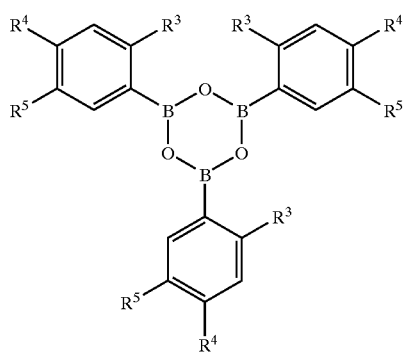

Suitable catalysts are, in particular, palladium catalysts such as tetrakis(triphenylphosphine)palladium(O), bis(triphenylphosphine)palladium(II) chloride, 1,4-bis(diphenylphosphino)-butanepalladium(II) chloride, 1,2-bis(diphenylphosphino)ethanepalladium(II) chloride, palladium(II) acetate+triphenylphosphine, palladium(II) acetate+tri(o-tolyl)phosphine or palladium on active charcoal, and nickel catalysts such as bis(triphenylphosphine)nickel(II) chloride, 1,3-bis(diphenylphosphino)propanenickel(II) chloride or nickel(II) acetylacetonate.

Process D

Reduction of 5-nitro-2-phenylpyridines of the formula V to give 5-amino-2-phenylpyridines VI, diazotization of the amino group and reaction of the diazonium salts with a symmetric aliphatic disulfide of the formula VII in a manner known per se:

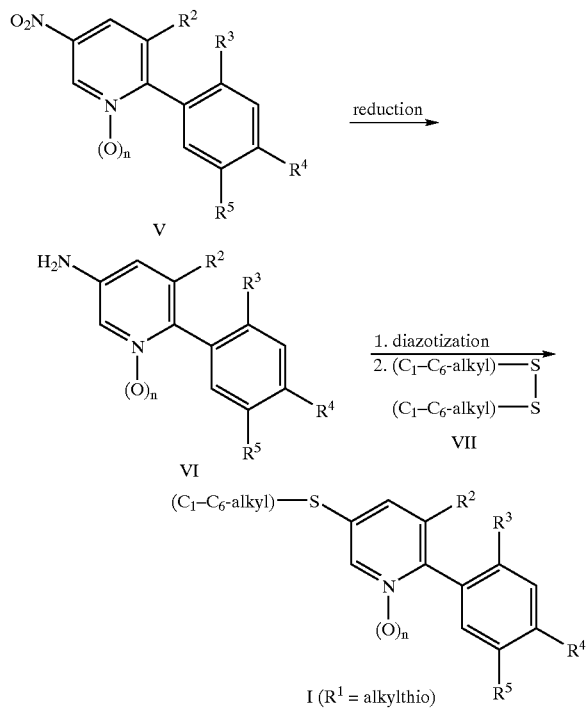

Reactions of this type are generally known, for example from the following publications:

Reduction of nitropyridines with hydrogen: F. Janssens et al., J. Med. Chem. 28(12) (1985), p. 1943;

Reduction of nitropyridines with iron: B. A. Fox et al., Org. Synth. 44 (1964), p. 34;

Reduction of nitropyridines with tin(II) chloride: L. A. Perez-Medina et al., J. Am. Chem. Soc. 69 (1947), p. 2574;

Reduction of nitropyridines with hydrazine: G. J. Clark et al., Aust. J. Chem. 34 (1981), p. 927;

Reduction of nitropyridines with tin: K. Wojciechowski et al., Synthesis 8 (1986), 651–653;

Reduction of nitropyridines with low-valency titanium compounds: M. Malinowski, B. Soc. Chim. Belg. 97(1) (1988), 51–53;

Reduction of nitropyridines with baker's yeast: M. Takeshita et al., Heterocycles 31(12) (1990), 2201–2204;

Reduction of nitropyridines with zinc: K. Goerlitzer et al., Arch. Pharm. 324(10) (1991), 785–796;

Reduction of nitropyridines with sodium dithionite: F. G. Fischer et al., Ann. Chem. 651 (1962), p. 49;

Diazotization of aminopyridines with isoamyl nitrite and reaction of the diazonium salts with dimethyl disulfide or diphenyl disulfide: C. S. Giam et al., J. Chem. Soc., Chem. Commun. 16 (1980), p. 756; T. Yasumitsu et al., J. Org. Chem. 46, 3564–3567 (1981).

2-(4-Chloro-3-methoxyphenyl)-5-nitropyridine, 2-(4-chloro-3-methoxyphenyl)-3-chloro-5-nitropyridine, 5-amino-2-(4-chloro-3-methoxyphenyl)pyridine and 5-amino-2-(4-chloro-3-methoxyphenyl)-3-chloropyridine have already been disclosed in WO 95/02580. Apart from these compounds, the 5-nitro-2-phenylpyridines V and the 5-amino-2-phenylpyridines VI are novel. The preparation of V is expediently carried out by a method similar to process C) by a transition-metal-catalyzed cross-coupling reaction of 2-halo-5-nitropyridines of the formula VIII (Hal=chlorine or bromine) with organometallic compounds of the formula IX {cf., for example, M. B. Mitchell et al., Tetrahedron Lett. 32 (1991), 2273–2276}:

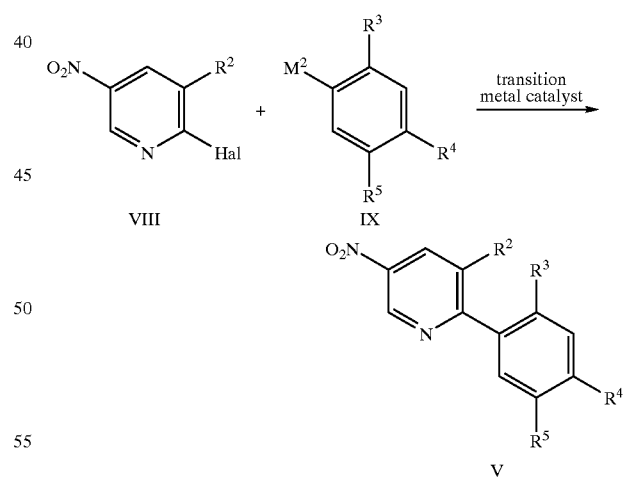

$M^2$ is $B(OH)_2$, Zn—Cl, Zn—Br, Zn—I, copper or tin-tri($C_1$–$C_4$-alkyl).

The catalysts given for process C) are also suitable in this context.

Process E

Diazotization of 5-amino-2-phenylpyridines of the formula VI and reaction of the diazonium salts with $SO_2$ in the presence of copper(II) chloride {cf., for example, U.S. Pat. No. 4,784,684 and Gilbert in Synthesis 1969, p. 6}:

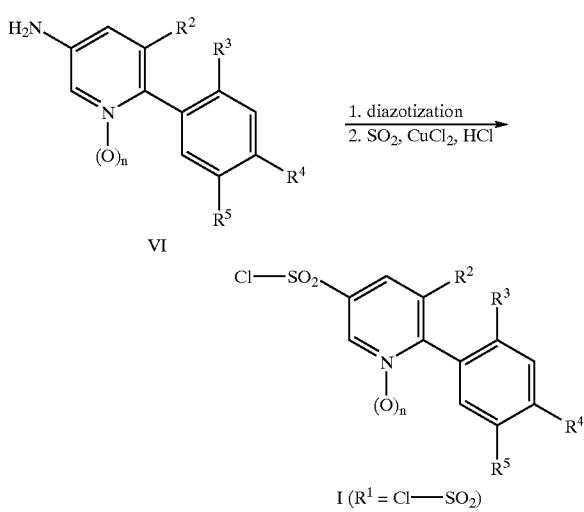

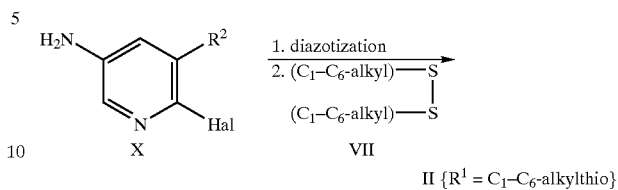

II {$R^1$ = $C_1$–$C_6$-alkylthio}

The reaction of I ($R^1$=$SO_2Cl$) with ammonia, primary or secondary amines leads to the corresponding compounds I where $R^1$=$H_2N$—$SO_2$, alkyl-NH—$SO_2$ or (alkyl)$_2$N—$SO_2$ {cf., for example, C. Naegeli et al., Helv. Chim. Acta 25 (1942), 1485; M. Yasuhiro et al., J. Med. Chem. 23 (1980), 1376–1380; J. F. Liegeois et al., Helv. Chim. Acta 74 (1991), 8, 1764–1772 and P. De Tullio et al., Tetrahedron 51 (1995), 11, 3221–3234}:

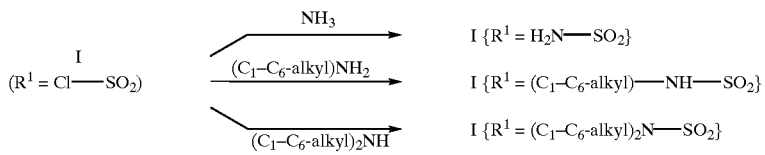

Moreover, the substituted 2-phenylpyridines I where $R^1$=chlorosulfonyl can also be hydrolyzed to give the corresponding compounds I where $R^1$=hydroxysulfonyl.

The substituted 2-phenylpyridines I can normally be prepared by one of the abovementioned synthesis processes. However, it may be more expedient for economic or process engineering reasons to prepare some compounds I from similar 2-phenylpyridines, which, however, differ in the meaning of one radical.

The compounds of the formula IIa

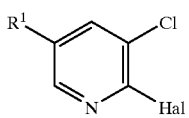

IIa are novel. 2-Chloro-5-methylthiopyridine is known, for example, from J. Med. Chem. 16 (1973), 319–327. As regards 2-chloro-5-methylsulfinyl- and 2-chloro-5-methylsulfonylpyridine, cf. J. Med. Chem. 29 (1986), 427–433; as regards 2-bromo-5-tert-butylthiopyridine, reference may be made to Bull. Soc. Chim. Belg. 95 (1986), 1009–1020.

In general, the preparation of the 2-halopyridines II can be carried out for example by diazotizing the corresponding 5-aminopyridines X [1]—preferably with a nitrous ester such as tert-butyl nitrite and isopentyl nitrite—and subsequently reacting the diazonium salt with a symmetric aliphatic disulfide VII {cf., for example, J. Chem. Soc., Chem. Commun. 1980, p. 756–757}:

[1] Re the preparation thereof, see J. Med. Chem. 16, 319–327 (1973)

The diazotization can be also carried out in the presence of the disulfide VII.

The process is preferably carried out in an anhydrous system, for example in glacial acetic acid which contains hydrogen chloride, in dioxane, absolute ethanol, tetrahydrofuran, acetonitrile, or in acetone.

The reaction temperature is normally at from (–30) to 80° C.

The components in the diazotization reaction are usually employed in an approximately stoichiometric ratio, but an excess of one of the components may also be advantageous, for example with a view to as complete a reaction as possible of the other components. It is preferred to use an excess of nitrite, up to approximately twice the molar amount, based on the amount of X.

The disulfide VII is expediently employed in approximately equimolar amounts or in an excess, based on the diazonium salt. In general, a large excess of disulfide VII (up to approximately 5 times the molar amount), based on the amount of diazonium salt, has proved to be especially advantageous.

The 2-halopyridines II where $R^1$=$C_1$–$C_6$-alkylthio can subsequently be oxidized to give the corresponding compounds where $R^1$=$C_1$–$C_6$-alkylsulfinyl or $C_1$–$C_6$-alkylsulfonyl, as described under process B) for the compounds I where $R^1$=$C_1$–$C_6$-alkylthio.

Unless otherwise specified, all the above-described processes are expediently carried out under atmospheric pressure or under the inherent pressure of the reaction mixture in question.

As a rule, the reaction mixtures are worked up by methods known per se, for example diluting the reaction solution with water and subsequently isolating the product by means of filtration, crystallization or solvent extraction, or removing the solvent, partitioning the residue in a mixture of water and a suitable organic solvent and working up the organic phase to give the product.

The substituted 2-phenylpyridines I can be obtained upon preparation in the form of isomer mixtures, but, if desired, these can be separated into the essentially pure isomers by the methods conventionally used for this purpose, such as crystallization or chromatography, also on an optically active absorbent. Pure, optically active isomers can be prepared advantageously from corresponding optically active starting materials.

Agriculturally useful salts of the compounds I can be formed by means of a reaction with a base of the corresponding cation, preferably an alkali metal hydroxide or alkali metal hydride.

Salts of I whose metal ion is not an alkali metal ion can also be prepared in a customary manner by double decomposition of the corresponding alkali metal salt, and also ammonium, phosphonium, sulfonium and sulfoxonium salts by means of ammonia, phosphonium hydroxide, sulfonium hydroxide or sulfoxonium hydroxide.

The compounds I and their agriculturally useful salts, not only as isomer mixtures but also in the form of the pure isomers, are suitable as herbicides. The herbicidal compositions comprising I effect very good control of vegetation on non-crop areas, especially at high rates of application. In crops such as wheat, rice, maize, soybeans and cotton, they are active against broad-leaved weeds and grass weeds without inflicting any appreciable damage on the crop plants. This effect occurs mainly at low rates of application.

Depending on the application method in question, the compounds I or herbicidal compositions comprising them can be employed in a further amount of crop plants for eliminating undesirable plants. Suitable crops are, for example, the following: *Allium cepa, Ananas comosus, Arachis hypogaea, Asparagus officinalis, Beta vulgaris* subsp. *altissima, Beta vulgaris* subsp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa , Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds I can also be used in crops which tolerate the action of herbicides as a result of breeding, including genetic engineering methods.

Moreover, the substituted 2-phenylpyridines I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is facilitating harvesting, which is made possible in citrus fruit, olives or other species and varieties of pomaceous fruit, stone fruit and nuts by concentrating, over a period of time, the adhesions or a reduced adhesion to the tree. The same mechanism, ie. promotion of the formation of abscission between fruit or leaf and shoot of the plants is also essential for readily controllable defoliation of crop plants, in particular cotton.

Moreover, the shortened period of time within which the individual cotton plants mature results in a better fiber quality after harvesting.

The compounds I or the compositions comprising them can be used, for example, in the form of directly sprayable aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or pouring. The use forms depend on the intended aims; in any case, they should guarantee the finest possible distribution of the active ingredients according to the invention.

Suitable inert auxiliaries are essential:

Mineral oil fractions of medium to high boiling point such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent tackifier, dispersant or emulsifier. Alternatively, it is possible to prepare concentrates composed of active substance, wetting agent, tackifier, dispersant or emulsifier and, if appropriate, solvent or oils, and these concentrates are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ethers, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active substances together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The concentrations of the active ingredients I in the ready-to-use preparations can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples which follow illustrate the preparation of such products:

I. 20 parts by weight of the compound No. Ia.181 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. Ia.384 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. Ia.402 are dissolved in a mixture composed of 25 parts by weight of cyclohexanone, 65 parts by weight of mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 2 are mixed thoroughly with 3 parts by weight of the sodium salt of diisobutylnaphthalene-α-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 3 are mixed with 97 parts by weight of finely divided kaolin. This gives a dust which comprises 3% by weight of the active ingredient.

VI. 20 parts by weight of the active ingredient No. 7 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active ingredient No. 10 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active ingredient No. 13 is dissolved in a mixture composed of 80 parts by weight of cyclohexanone and 20 parts by weight of Wettol® EM 31 (=non-ionic emulsifier based on ethoxylated castor oil; BASF AG). This gives a stable emulsion concentrate.

The active ingredients I or the herbicidal compositions can be applied pre- or post-emergence. If the active ingredients are less well tolerated by certain crop plants, application techniques may be used in which the herbicidal compositions are sprayed, with the aid of the spraying equipment, in such a way that they come into as little contact as possible, if any, with the leaves of the sensitive crop plants while reaching the leaves of undesirable plants which grow underneath, or the bare soil (post-directed, lay-by).

Depending on the intended aim of the control measures, the season, the target plants and the growth stage, the rates of application of active ingredient I are from 0.001 to 3.0, preferably 0.01 to 1.0, kg/ha of active substance (a.s.).

To widen the spectrum of action and to achieve synergistic effects, the substituted 2-phenylpyridines I can be mixed with a large number of representatives of other groups of active ingredients which have a herbicidal or growth-regulating action and then applied jointly. Components in mixtures are, for example, 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl)/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may also be advantageous to apply the compounds I, alone or in combination with other herbicides, as a mixture with a further number of crop protection agents, for example with pesticides or agents for controlling phytopathogenic fungi or bacteria. Of further interest is the miscibility with mineral salt solutions which are employed for treating nutritional and trace element deficiencies. Non-phytotoxic oils and oil concentrates may also be added.

PREPARATION EXAMPLES

Example 1

(Compound Ia.384 in Table 1)

12.1 g of (2,3-dichloro-5-methylsulfonylpyridine, 11.05 g of 4-chloro-2-fluoro-5-methoxybenzeneboronic acid, 13.6 g of sodium hydrogen carbonate and 2.0 g of tetrakis (triphenylphosphine)palladium(0) were refluxed for 120 hours in 360 ml of a tetrahydrofuran/water mixture (1:1). After the mixture had cooled to room temperature, it was extracted three times using in each case 100 ml of methyl tert-butyl ether (MTB). The combined organic phases were washed with 100 ml of water, then dried over sodium sulfate and finally concentrated. The crude product was purified by means of column chromatography on silica gel (eluent: cyclohexane/MTB=10:1→7:3→1:1). The resulting white crystals (5.8 g) were further purified by stirring with MTB/petroleum ether (1:1). Yield: 5.2 g (27%); m.p.: 184–185° C.

Precursor α: 2,3-Dichloro-5-methylthiopyridine

A solution of 50.6 g (0.3 mol) of 3-amino-5,6-dichloropyridine in 700 ml of methylene chloride was slowly added dropwise at 40° C. to a solution of 56.6 g (0.6 mol) of dimethyl disulfide and 46.7 g (0.45 mol) of tert-butyl nitrite in 320 ml of dry methylene chloride. The mixture was then stirred for 1 hour at 40° C. and subsequently for another approximately 15 hours at approximately 20° C., whereupon 500 ml of ice-water were added to the reaction mixture. The organic phase which was separated off was washed once with 1 N hydrochloric acid and once with water, dried over sodium sulfate and finally concentrated. After the crude product had been stirred with n-hexane, 21 g of a dark solid were obtained (purity 94% according to GC). After the hexane solution was concentrated, a further 21.3 g of product of value remained which had a purity of 77% (according to GC). Total yield: 62%; m.p.: 66–67° C.; $^1$H-NMR (in $d^6$ dimethyl sulfoxide): δ [ppm]=2.6 (s, $CH_3$); 8.1 and 8.3 (2×d, pyr H).

Precursor β: 2,3-Dichloro-5-methylsulfinylpyridine 8.9 g (0.052 mol) of m-chloroperbenzoic acid were added, a little at a time, to a suspension of 10 g (0.052 mol) of 2,3-dichloro-5-methylthiopyridine in 60 ml of methylene chloride. After the mixture had been stirred for 2 hours at approximately 20° C., a further 0.9 g (5 mmol) of m-chloroperbenzoic acid was added. The mixture was subsequently refluxed for a further 2 hours. After cooling, the solids were separated off, whereupon the organic phase was washed once with sodium hydrogen sulfite, once with sodium hydrogen carbonate and once with water. After the mixture had been dried over sodium sulfate, it was concentrated. The crude product which was obtained as a red oil was purified by means of flash chromatography over silica gel (eluent: cyclohexane/ethyl acetate=1:1). Yield: 6.3 g (58%) as a brown oil; $^1$H-NMR (in $d^6$ dimethyl sulfoxide): δ [ppm]=2.9 (s, $CH_3$); 8.4 and 8.7 (2×d, pyr H).

Precursor γ: 2,3-Dichloro-5-methylsulfonylpyridine 6.2 g (0.02 mol) of $Na_2WO_4.2H_2O$ were added to a solution of 73.7 g (0.38 mol) of 2,3-dichloro-5-methylthiopyridine in 380 ml of glacial acetic acid. After the mixture had been heated to 40–50° C., 95 g of hydrogen peroxide (30% strength) were added carefully. Stirring was subsequently continued for a further hour at approximately 20° C. The mixture was then poured into 300 ml of water. The product was separated off from the resulting suspension, washed with water and n-pentane and dried under reduced pressure. Yield: 60 g (70%) as a brown powder; m.p.: 129–130° C.; $^1$H-NMR (in $d^6$ dimethyl sulfoxide): δ [ppm]= 3.4 (s, $CH_3$); 8.7 and 8.9 (2×d, pyr H).

Example 2

(Compound Ia.383 in Table 1)

4.15 g of compound Ia.384 which had been obtained as described in Example 1 and 10.2 g of pyridine hydrochloride were heated for four hours at 200° C. under a nitrogen atmosphere. After cooling, the reaction mixture was taken up in 100 ml of 10% strength hydrochloric acid. The product was then extracted five times using in each case 90 ml of dichloromethane. The combined organic phases were washed with 100 ml of water, dried over sodium sulfate and finally concentrated. The resulting crystals were purified by stirring with MTB/petroleum ether (1:1). After separation and drying, 3.6 g (90%) of white crystals were obtained; m.p.: 176–178° C.

Example 3

(Compound Ia.402 in Table 1)

0.52 g of propargyl bromide was added dropwise to 1.2 g of the compound Ia.383 which had been prepared as described in Example 2 and 0.99 g of potassium carbonate in 80 ml of anhydrous dimethylformamide. After the mixture had been stirred for twelve hours at 23° C., it was diluted with 200 ml of water. The product was then extracted four times using in each case 100 ml of MTB. The combined organic phases were washed with 100 ml of water, dried over sodium sulfate and finally concentrated. The crude product was purified by stirring with n-hexane/diethyl ether (10:1). After separation and drying, 0.9 g (67%) of white crystals was obtained; m.p.: 182–183° C.

Example 4

(Compound Ia.182 in Table 1; (R) enantiomer)

1.05 g of methyl (S)-2-chloropropionate were added dropwise to 2.4 g of the compound Ia.383 which had been prepared as described in Example 2 and 1.97 g of potassium carbonate in 100 ml of anhydrous dimethylformamide. After the mixture had been stirred for sixty hours at 23° C., it was diluted with 300 ml of water. The product was then extracted four times using in each case 80 ml of MTB. The combined organic phases were washed with 100 ml of water, dried over sodium sulfate and finally concentrated. The crude product was purified by means of chromatography on silica gel (eluent: cyclohexane/MTB=5:1→7:1). Yield: 2.6 g (86%) of a colorless oil.

$^1$H-NMR (200 MHz; in $CDCl_3$): δ [ppm]=1.70 (d, 3H), 3.20 (s, 3H), 3.77 (s, 3H), 4.78 (q, 1H), 7.00 (d, 1H), 7.28 (d, 1H), 8.33 (s, 1H), 9.07 (s, 1H).

Example 5

(Compound Ia.181 in Table 1; (R) enantiomer)

1.2 g of the compound Ia.182 which had been prepared as described in Example 4 were stirred for 4 hours at 70 to 80° C. and subsequently for 16 hours at 23° C. in a mixture of 25 ml of glacial acetic acid and 10 ml of 2 M hydrochloric acid. After the mixture had been diluted with 100 ml of water, it was extracted five times with in each case 60 ml of MTB. The combined organic phases were washed twice with in each case 60 ml of saturated aqueous sodium chloride solution, then dried over sodium sulfate and finally concentrated. The crude product was purified by stirring with n-hexane/diethyl ether (2:1). Yield: 0.75 g (65%) of white crystals; m.p.: 161–164° C.

Example 6

3-Chloro-2-(4-chloro-2-fluoro-5-methoxyphenyl)-5-methylsulfinylpyridine 4.6 g of 2,3-dichloro-5-methylsulfinylpyridine, 4.5 g of 4-chloro-2-fluoro-5-methoxybenzeneboronic acid, 5.5 g of sodium hydrogen carbonate and 1.0 g of tetrakis (triphenylphosphine)palladium(0) were refluxed for 180 hours in a mixture of 100 ml of water and 100 ml of tetrahdyrofuran. After the tetrahydrofuran has been evaporated, the residue was extracted four times with in each case 70 ml of MTB. The combined organic phases were then dried over sodium sulfate and finally concentrated. The resulting oil was purified by means of chromatography on silica gel (eluent: cyclohexane/MTB=7:3→1:1 and cyclohexane/ethyl acetate=2:1). Stirring this purified oil with diethyl ether gave 2.2 g (30%) of white crystals.; m.p.: 117–118° C.

Example 7

Preparation of the Precursor 2,3-Dichloro-5-ethylsulfonylpyridine 5 g (0.024 mol) of 2,3-dichloro-5-ethylthiopyridine were reacted with 0.4 g (1.2 mmol) of $Na_2WO_4.2H_2O$ and 6 g of hydrogen peroxide (30% strength) in 25 ml of glacial acetic acid by a method similar to Example 1, Precursor γ. After working up, 5.1 g of product of value were obtained as a white solid.

Yield: 88.5%; m.p.: 141–142° C.; $^1$H-NMR (in d$^6$ dimethyl sulfoxide): δ [ppm]=1.2 (t, CH$_3$); 3.5 (q, CH$_2$); 8.6 and 8.8 (2×d, pyr H).

Precursor α: 2,3-Dichloro-5-ethylthiopyridine 24.45 g (0.15 mol) of 3-amino-5,6-dichloropyridine in 280 ml of methylene chloride were reacted with 36.6 g (0.3 mol) of diethyl disulfide and 23.2 g (0.225 mol) of tert-butyl nitrite in 130 ml of methylene chloride by a method similar to Example 1, Precursor α. After working up and subsequently washing the crude product with ethanol, 13.3 g of product of value were obtained.

Yield: 42%; $^1$H-NMR (in d$^6$ dimethyl sulfoxide): δ [ppm]=1.25 (t, CH$_3$); 3.10 (d, CH$_2$); 8.15 and 8.3 (2×d, pyr H).

Precursor β: 2,3-Dichloro-5-ethylsulfinylpyridine 4 g (0.02 mol) of 2,3-dichloro-5-ethylthiopyridine were reacted with 3.47 g (0.02 mol) of m-chloroperbenzoic acid in 30 ml of methylene chloride by a method similar to Example 1, Precursor β. After the crude product had been purified by means of flash chromatography on silica gel (eluent: cyclohexane/ethyl acetate=2:1), 1.9 g of product of value were obtained in the form of white crystals. Yield: 42%. m.p.: 78–79° C.; $^1$H-NMR (d$^6$ dimethyl sulfoxide): δ [ppm]=1.1 (t; CH$_3$); 3.0 and 3.2 (2×m, CH$_2$); 8.35 and 8.6 (2×s, pyr H).

Example 8

Preparation of the Precursor 2,3-Dichloro-5-isopropylsulfonylpyridine 15 g (0.068 mol) of 2,3-dichloro-5-isopropylthiopyridine (crude product) were reacted with 1.11 g (3.6 mmol) of Na$_2$WO$_4$·2H$_2$O and 17 g of hydrogen peroxide (30% strength) in 80 ml of acetic acid by a method similar to Example 1, Precursor γ. After working up and additional stirring the crude product with ethanol, 3.5 g of product of value were obtained as a pale powder. Yield: 20%; m.p.: 146° C.; $^1$H-NMR (in d$^6$ dimethyl sulfoxide): δ [ppm]=1.2 (d, 2×CH$_3$); 3.65 (m, CH); 8.6 and 8.8 (2×d, pyr H).

Precursor α: 2,3-Dichloro-5-isopropylthiopyridine 13.1 g (0.08 mol) of 3-amino-5,6-dichloropyridine in 120 ml of methylene chloride were reacted with 25 g (0.16 mol) of diisopropyl disulfide and 12.4 g (0.12 mol) of tert-butyl nitrite in 70 ml of methylene chloride by a method similar to Example 1, Precursor α. This gave 30 g of the dark oil (approximately 40% of product of value) which was further reacted without further purification. $^1$H-NMR (in d$^6$ dimethyl sulfoxide): δ [ppm]=1.25 (d, 2×CH$_3$); 3.7 (m, CH); 8.2 and 8.3 (2×d, pyr H).

Precursor β: 2,3-Dichloro-5-isopropylsulfinylpyridine 10 g (0.045 mol) of 2,3-dichloro-5-isopropylthiopyridine (as crude product) were reacted with 7.8 g (0.045 mol) of m-chloroperbenzoic acid in 60 ml of methylene chloride by a method similar to Example 1, Precursor β. After the crude product had been purified by means of flash chromatography on silica gel (eluent: cyclohexane/ethyl acetate 1:1), 1.7 g of product of value were obtained. Yield: 16%; m.p.: 62–64° C.; $^1$H-NMR (in d$^6$ dimethyl sulfoxide): δ [ppm]=1.0 and 1.25 (2×d, 2×CH$_3$); 3.2 (m, CH); 8.3 and 8.5 (2×d, pyr H).

Other substituted 2-phenylpyridines I are listed in Table 2 below:

TABLE 2

I

{n = 0}

| No. | R$^1$ | R$^2$ | R$^3$ | R$^4$ | R$^5$ | Physical data (m.p.) |
|---|---|---|---|---|---|---|
| 1 | SCH$_3$ | Cl | F | Cl | OH | 164° C. |
| 2 | SCH$_3$ | Cl | F | Cl | OCH$_3$ | 102° C. |
| 3 | SC$_2$H$_5$ | Cl | F | Cl | OCH$_3$ | 94° C. |
| 4 | SCH(CH$_3$)$_2$ | Cl | F | Cl | OCH$_3$ | oil |
| 5 | SO—CH$_3$ | Cl | F | Cl | OH | 163° C. |
| 6 | SO—CH$_3$ | Cl | F | Cl | OCH$_3$ | 118° C. |
| 7 | SO—CH$_3$ | Cl | F | Cl | OCH$_2$—C≡CH | 145° C. |
| 8 | SO—C$_2$H$_5$ | Cl | F | Cl | OCH$_3$ | oil |
| 9 | SO—CH(CH$_3$)$_2$ | Cl | F | Cl | OCH$_3$ | 138° C. |
| 10 | SO$_2$—C$_2$H$_5$ | Cl | F | Cl | OCH$_3$ | 147° C. |
| 11 | SO$_2$—CH(CH$_3$)$_2$ | Cl | F | Cl | OCH$_3$ | 120° C. |
| 12 | SCH$_3$ | Cl | H | Cl | OH | 101° C. |
| 13 | SCH$_3$ | Cl | Cl | Cl | OCH$_3$ | 115° C. |
| 14 | SCH$_3$ | Cl | H | OCH$_3$ | H | 90° C. |
| 15 | SO—CH$_3$ | H | F | Cl | OCH$_3$ | 137° C. |
| 16 | SO$_2$—CH$_3$ | H | F | Cl | OCH$_3$ | 151° C. |
| 17 | SO$_2$—CH$_3$ | Cl | H | OH | H | 226° C. |
| 18 | SO$_2$—CH$_3$ | Cl | H | OH | NO$_2$ | 182° C. |

USE EXAMPLES

Herbicidal Activity

The herbicidal activity of the substituted 2-phenylpyridines I was demonstrated by the following greenhouse experiments:

The culture containers used were plastic flowerpots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active ingredients.

For the post-emergence treatment, the test plants were first grown to a height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 0.0313 or 0.0156 kg/ha a.s. (active substance).

Depending on the species, the plants were kept at from 10 to 25° C. and 20 to 35° C., respectively. The test period extended over 2 to 4 weeks. During this time, the plants were tended, and their response to individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific name | Common name |
| --- | --- |
| Abutilon theophrasti | velvet leaf |
| Chenopodium album | lambsquarters (goosefoot) |
| Solanum nigrum | black nightshade |
| Veronica species | speedwell |

At rate of applications of 0.0313 and 0.0156 kg/ha a.s., the compound No. Ia.384 showed a very good herbicidal activity against the abovementioned broad-leaved plants when applied post-emergence.

USE EXAMPLES

Desiccant/Defoliant Action

The test plants used were young cotton plants with 4 leaves (without cotyledons) which had been grown under greenhouse conditions (relative atmospheric humidity 50 to 70%; day/night temperature 27/20° C.).

The young cotton plants were given a foliar treatment to run-off point with aqueous preparations of the active ingredients (with addition of 0.15% by weight of the fatty alcohol alkoxide Plurafac® LF 700 [2], based on the spray mixture). The amount of water applied was 1000 l/ha (converted). After 13 days, the number of shed leaves and the degree of defoliation in % were determined.

[2] A low-foam, nonionic surfactant by BASF AG

No leaves were shed in the untreated control plants.

We claim:

1. A substituted 2-phenylpyridine of the formula I

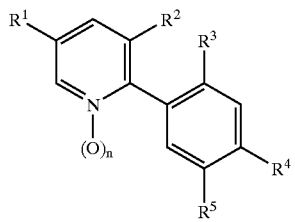

in which the variables have the following meanings:
n is zero;
$R^1$ is $C_1$–$C_6$-alkylsulfinyl or $C_1$–$C_6$-alkylsulfonyl;
$R^2$ is halogen;
$R^3$ is hydrogen or halogen;
$R^4$ is cyano or halogen;
$R^5$ is hydrogen, nitro, cyano, hydroxylamino, $C_1$–$C_6$-alkyl, $C_1$–$C_6$-haloalkyl, —COCl, —CO—$OR^6$, —CO—O—($C_1$–$C_4$-alkylene)—CO—$OR^6$, —O—($C_1$–$C_4$-alkylene)—CO—$OR^6$, —O—($C_1$–$C_4$-alkylene)—CO—O—($C_1$–$C_4$-alkylene)—CO—$OR^6$, —$OR^9$, formyl, —CH=N—$OR^{15}$, —N($R^{16}$)$R^{17}$, —N($R^{16}$)—$SO_2$—($C_1$–$C_6$-alkyl) or —N($R^{16}$)—CO—($C_1$–$C_6$-alkyl);

$R^6$ is hydrogen, $C_1$–$C_6$-alkyl, $C_3$–$C_6$-alkenyl, $C_3$–$C_6$-alkynyl or $C_1$–$C_6$-alkoxy-$C_1$–$C_6$-alkyl;

$R^9$ is hydrogen, $C_1$–$C_6$-alkyl, $C_3$–$C_6$-alkenyl or $C_3$–$C_6$-alkynyl;

$R^{15}$ is $C_1$–$C_6$-alkyl;

$R^{16}$ is hydrogen or $C_1$–$C_6$-alkyl;

$R^{17}$ is hydrogen, $C_1$–$C_6$-alkyl, hydroxycarbonyl-$C_1$–$C_6$-alkyl, ($C_1$–$C_6$-alkoxy)carbonyl-$C_1$–$C_6$-alkyl or $C_1$–$C_6$-alkoxy;

or an agriculturally useful salt of a compound I where $R^6$=hydrogen.

2. A herbicidal composition which comprises a herbicidally active amount of at least one substituted 2-phenylpyridine of the formula I or of an agriculturally useful salt of I, as claimed in claim 1, and at least one inert liquid and/or solid carrier and, optionally, at least one surfactant.

3. A composition for the desiccation and/or defoliation of plants comprising such an amount of at least one substituted 2-phenylpyridine of the formula I or of an agriculturally useful salt of I, as claimed in claim 1, that it acts as a desiccant and/or defoliant, and at least one inert liquid and/or solid carrier and, optionally, at least one surfactant.

4. A method of controlling undesirable vegetation, which comprises allowing a herbicidally active amount of at least one substituted 2-phenylpyridine of the formula I or of an agriculturally useful salt of I, as claimed in claim 1, to act on plants, their environment or on seed.

5. A method for the desiccation and/or defoliation of plants, which comprises allowing such an amount of at least one substituted 2-phenylpyridine of the formula I or of an agriculturally useful salt of I, as claimed in claim 1, to plants, that it acts as a desiccant and/or defoliant.

6. A method as claimed in claim 5, wherein cotton is treated.

7. The substituted 2-phenylpyridine of claim 1, where n=0, $R^1$=methylsulfonyl, $R^2$ and $R^4$=chlorine, $R^3$=fluorine and $R^5$=—$OCH_3$.

8. A process for the preparation of substituted 2-phenylpyridines of the formula I as claimed in claim 1 where $R^1$ is $C_1$–$C_6$-alkylthio, which comprises reducing 5-nitro-2-phenylpyridines of the formula V

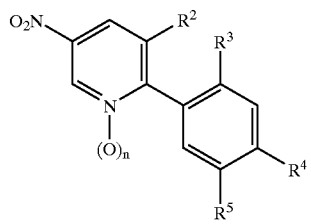

where n and $R^2$ to $R^5$ have the meanings given in claim 1, diazotizing the resulting 5-amino-2-phenylpyridines of the formula VI

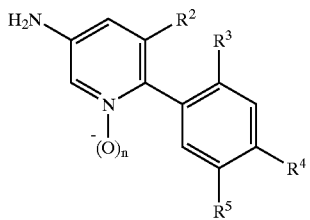

VI and finally reacting the diazonium salts with symmetrical aliphatic disulfides of the formula VII $$(C_1\text{–}C_6\text{-alkyl})\text{—S—S—}(C_1\text{–}C_6\text{-alkyl}) \qquad \text{VII.}$$

9. The substituted 2-phenylpyridine of claim 1, where $R^1$ is $C_1$–$C_6$-alkylsulfonyl.

10. The substituted 2-phenylpyridine of claim 1, where $R^5$ is hydrogen, nitro, cyano, hydroxylamino, $C_1$–$C_6$-alkyl, $C_1$–$C_6$-haloalkyl, —COCl, —CO—$OR^6$, —CO—O—($C_1$–$C_4$-alkylene)—CO—$OR^6$, —O—($C_1$–$C_4$-alkylene)—CO—$OR^6$, —O—($C_1$–$C_4$-alkylene)—CO—O—($C_1$–$C_4$-alkylene)—CO—$OR^6$, —$OR^9$, formyl, —CH=N—$OR^{15}$ or —$NH_2$.

* * * * *